US012735419B2

(12) United States Patent
Beaver et al.

(10) Patent No.: US 12,735,419 B2
(45) Date of Patent: Sep. 15, 2026

(54) PROCESS FOR RACEMIZING AND ISOLATING ATROPISOMERS OF 7-CHLORO-6-FLUORO-1-(2-ISOPROPYL-4-METHYLPYRIDIN-3-YL)PYRIDO [2,3-D]PYRIMIDINE-2,4(1H,3H)-DIONE

(71) Applicant: AMGEN INC., Thousand Oaks, CA (US)

(72) Inventors: Matthew G. Beaver, Natick, MA (US); Michael T. Corbett, San Carlos, CA (US); Yuanqing Fang, Belmont, MA (US); David D. Ford, Cambridge, MA (US); Andrew T. Parsons, Cambridge, MA (US); Gabrielle St-Pierre, Thousand Oaks, CA (US); Reem Telmesani, Brighton, MA (US)

(73) Assignee: Amgen Inc., Thousand Oaks, CA (US)

( * ) Notice: Subject to any disclaimer, the term of this patent is extended or adjusted under 35 U.S.C. 154(b) by 551 days.

(21) Appl. No.: 18/030,685

(22) PCT Filed: Oct. 6, 2021

(86) PCT No.: PCT/US2021/053859

§ 371 (c)(1),
(2) Date: Apr. 6, 2023

(87) PCT Pub. No.: WO2022/076623

PCT Pub. Date: Apr. 14, 2022

(65) Prior Publication Data

US 2023/0391771 A1 Dec. 7, 2023

Related U.S. Application Data

(60) Provisional application No. 63/162,278, filed on Mar. 17, 2021, provisional application No. 63/088,848, filed on Oct. 7, 2020.

(51) Int. Cl.
*C07D 471/04* (2006.01)

(52) U.S. Cl.
CPC ........ *C07D 471/04* (2013.01); *C07B 2200/07* (2013.01); *C07B 2200/13* (2013.01)

(58) Field of Classification Search
CPC .................................................... C07D 471/04
USPC .......................................................... 544/279
See application file for complete search history.

(56) References Cited

U.S. PATENT DOCUMENTS 4,232,027 A 11/1980 Turk et al.
5,100,883 A 3/1992 Schiehser
5,112,946 A 5/1992 Maione
5,118,677 A 6/1992 Caufield
5,118,678 A 6/1992 Kao et al.
5,120,842 A 6/1992 Failli et al.
5,151,413 A 9/1992 Caufield et al.
5,256,790 A 10/1993 Nelson
5,258,389 A 11/1993 Goulet et al.
5,455,258 A 10/1995 Macpherson et al.
5,521,184 A 5/1996 Zimmermann
5,616,582 A 4/1997 Barker
5,650,415 A 7/1997 Tang et al.
5,656,643 A 8/1997 Spada et al.
5,712,291 A 1/1998 D Amato
5,728,813 A 3/1998 Lyman et al.
5,741,907 A 4/1998 Baiocchi et al.
5,747,498 A 5/1998 Schnur et al.
5,770,599 A 6/1998 Gibson
5,789,427 A 8/1998 Chen et al.
5,792,783 A 8/1998 Tang et al.
5,824,729 A 10/1998 Matsushita et al.
5,861,510 A 1/1999 Piscopio et al.

(Continued)

FOREIGN PATENT DOCUMENTS

AU 18422/92 A 1/1993
CA 2210056 A1 1/1998

(Continued)

OTHER PUBLICATIONS

International Search Report and Written Opinion of the International Search Authority, European Patent Office, PCT/US2021/053859, dated Jan. 20, 2022.

(Continued)

*Primary Examiner* — Niloofar Rahmani

(74) *Attorney, Agent, or Firm* — Matthew Duffey

(57) ABSTRACT

Provided herein is a process comprising heating a composition comprising (P)-compound A or a salt thereof and a solvent to a temperature of 250° C. to 350° C. to form racemized compound A. Also provided is a process for isolating (P)-compound A from a composition comprising (P)-compound A and a tartrate, as described herein. Further provided herein, is a process for isolating a free acid of a tartrate or a hydrate thereof from a composition comprising a tartrate, (P)-compound A, and an organic solvent.

(A)

26 Claims, No Drawings

(56) References Cited

U.S. PATENT DOCUMENTS

| | | | |
|---|---|---|---|
| 5,863,949 | A | 1/1999 | Robinson et al. |
| 5,892,112 | A | 4/1999 | Levy et al. |
| 5,969,110 | A | 10/1999 | Beckmann et al. |
| 5,981,245 | A | 11/1999 | Fox et al. |
| 5,990,141 | A | 11/1999 | Hirth et al. |
| 6,001,961 | A | 12/1999 | Jonczyk et al. |
| 6,057,124 | A | 5/2000 | Bartley et al. |
| 6,090,852 | A | 7/2000 | Dack et al. |
| 6,096,749 | A | 8/2000 | Traxler et al. |
| 6,111,090 | A | 8/2000 | Gorman et al. |
| 6,114,361 | A | 9/2000 | Robinson et al. |
| 6,232,447 | B1 | 5/2001 | Cerretti |
| 6,235,764 | B1 | 5/2001 | Larson et al. |
| 6,258,812 | B1 | 7/2001 | Bold et al. |
| 6,323,208 | B1 | 11/2001 | Chenard et al. |
| 6,413,932 | B1 | 7/2002 | Cerretti et al. |
| 6,515,004 | B1 | 2/2003 | Misra et al. |
| 6,596,852 | B2 | 7/2003 | Cerretti et al. |
| 6,630,500 | B2 | 10/2003 | Gingrich et al. |
| 6,656,963 | B2 | 12/2003 | Firestone et al. |
| 6,713,485 | B2 | 3/2004 | Carter et al. |
| 6,727,225 | B2 | 4/2004 | Wiley |
| 7,025,962 | B1 | 4/2006 | Gorman et al. |
| 7,358,384 | B2 | 4/2008 | Morii et al. |
| 7,361,760 | B2 | 4/2008 | Sircar et al. |
| 7,618,632 | B2 | 11/2009 | Collins et al. |
| 7,812,135 | B2 | 10/2010 | Smith et al. |
| 7,838,700 | B2 | 11/2010 | Martin et al. |
| 8,388,967 | B2 | 3/2013 | Smith et al. |
| 8,586,023 | B2 | 11/2013 | Shiku et al. |
| 8,591,886 | B2 | 11/2013 | Ponath et al. |
| 10,519,146 | B2 | 12/2019 | Lanman |
| 10,532,042 | B2 | 1/2020 | Lanman |
| 10,640,504 | B2 | 5/2020 | Lanman et al. |
| 10,988,485 | B2 | 4/2021 | Minatti et al. |
| 11,045,484 | B2 | 6/2021 | Wurz et al. |
| 11,053,226 | B2 | 7/2021 | Shin et al. |
| 11,090,304 | B2 | 8/2021 | Allen et al. |
| 11,096,939 | B2 | 8/2021 | Booker et al. |
| 11,285,135 | B2 | 3/2022 | Lanman |
| 11,299,281 | B2 | 4/2022 | Holstine et al. |
| 11,299,491 | B2 | 4/2022 | Parsons et al. |
| 11,905,281 | B2 | 2/2024 | Lanman et al. |
| 12,391,689 | B2 | 8/2025 | Parsons et al. |
| 12,391,691 | B2 | 8/2025 | Parsons et al. |
| 12,441,729 | B2 | 10/2025 | Achmatowicz et al. |
| 12,459,896 | B2 | 11/2025 | Smith et al. |
| 12,466,825 | B2 | 11/2025 | Parsons et al. |
| 12,473,281 | B2 | 11/2025 | Corbett et al. |
| 2002/0042368 | A1 | 4/2002 | Fanslow et al. |
| 2002/0091261 | A1 | 7/2002 | Bold et al. |
| 2003/0105091 | A1 | 6/2003 | Riedl et al. |
| 2003/0162712 | A1 | 8/2003 | Cerretti et al. |
| 2004/0063658 | A1 | 4/2004 | Roberts et al. |
| 2005/0085665 | A1 | 4/2005 | Martin et al. |
| 2009/0012085 | A1 | 1/2009 | Baum et al. |
| 2011/0059109 | A1 | 3/2011 | Smith et al. |
| 2012/0263706 | A1 | 10/2012 | Cui et al. |
| 2014/0288045 | A1 | 9/2014 | Ren et al. |
| 2015/0239900 | A1 | 8/2015 | Li et al. |
| 2016/0159738 | A1 | 6/2016 | Ren et al. |
| 2016/0166571 | A1 | 6/2016 | Janes et al. |
| 2016/0297774 | A1 | 10/2016 | Li et al. |
| 2018/0015087 | A1 | 1/2018 | Liu et al. |
| 2018/0072723 | A1 | 3/2018 | Blake et al. |
| 2018/0177767 | A1 | 6/2018 | Lanman et al. |
| 2018/0334454 | A1 | 11/2018 | Lanman et al. |
| 2019/0077801 | A1 | 3/2019 | Lanman et al. |
| 2019/0336514 | A1 | 11/2019 | Wurz et al. |
| 2019/0343838 | A1 | 11/2019 | Allen et al. |
| 2019/0345169 | A1 | 11/2019 | Minatti et al. |
| 2019/0374542 | A1 | 12/2019 | Allen et al. |
| 2019/0375749 | A1 | 12/2019 | Chen et al. |
| 2020/0030324 | A1 | 1/2020 | Booker et al. |
| 2020/0055845 | A1 | 2/2020 | Lanman |
| 2020/0069657 | A1 | 3/2020 | Lanman et al. |
| 2020/0165231 | A1 | 5/2020 | Shin et al. |
| 2020/0207766 | A1 | 7/2020 | Lanman et al. |
| 2020/0216446 | A1 | 7/2020 | Parsons et al. |
| 2020/0222407 | A1 | 7/2020 | Lipford et al. |
| 2020/0360374 | A1 | 11/2020 | Henary et al. |
| 2020/0369662 | A1 | 11/2020 | Chaves et al. |
| 2021/0009577 | A1 | 1/2021 | Lanman |
| 2022/0168280 | A1 | 6/2022 | Lanman |
| 2022/0220112 | A1 | 7/2022 | Parsons et al. |
| 2023/0192681 | A1 | 6/2023 | Parsons |
| 2023/0192682 | A1 | 6/2023 | Corbett |
| 2024/0025896 | A1 | 1/2024 | Achmatowicz et al. |
| 2024/0174660 | A1 | 5/2024 | Lanman et al. |
| 2025/0122197 | A1* | 4/2025 | Beaver ................ C07D 471/04 |
| 2025/0129072 | A1 | 4/2025 | Achmatowicz et al. |
| 2025/0179068 | A1 | 6/2025 | Parsons et al. |
| 2025/0188036 | A1 | 6/2025 | Smith et al. |
| 2025/0206705 | A1 | 6/2025 | Smith et al. |
| 2025/0206735 | A1 | 6/2025 | Parsons et al. |
| 2025/0206736 | A1 | 6/2025 | Corbett et al. |
| 2025/0368642 | A1 | 12/2025 | Parsons et al. |
| 2025/0368643 | A1 | 12/2025 | Parsons et al. |
| 2025/0388579 | A1 | 12/2025 | Parsons et al. |
| 2026/0028339 | A1 | 1/2026 | Corbett et al. |

FOREIGN PATENT DOCUMENTS

| | | | |
|---|---|---|---|
| CA | 2218945 | A1 | 4/1998 |
| CN | 101239913 | A | 8/2008 |
| DE | 19629652 | A1 | 1/1998 |
| EA | 201690752 | A1 | 7/2016 |
| EA | 201792214 | A1 | 1/2018 |
| EP | 0090505 | A2 | 10/1983 |
| EP | 0407122 | A1 | 1/1991 |
| EP | 0520722 | A1 | 12/1992 |
| EP | 0566226 | A1 | 10/1993 |
| EP | 0606046 | A1 | 7/1994 |
| EP | 0682027 | A1 | 11/1995 |
| EP | 0770622 | A2 | 5/1997 |
| EP | 0780386 | A1 | 6/1997 |
| EP | 0787772 | A2 | 8/1997 |
| EP | 0818442 | A2 | 1/1998 |
| EP | 0837063 | A1 | 4/1998 |
| EP | 0931788 | A2 | 7/1999 |
| EP | 0970070 | A1 | 1/2000 |
| EP | 1004578 | A2 | 5/2000 |
| EP | 1181017 | A1 | 2/2002 |
| EP | 1786785 | A2 | 5/2007 |
| EP | 1866339 | A2 | 12/2007 |
| EP | 1947183 | A1 | 7/2008 |
| EP | 1446372 | B1 | 4/2009 |
| EP | 3055290 | A1 | 8/2016 |
| EP | 3401314 | A1 | 11/2018 |
| GB | 2116183 | A | 9/1983 |
| JP | 02-233610 | A | 9/1990 |
| JP | 09-176115 | A | 7/1997 |
| JP | 2005-509011 | A | 4/2005 |
| JP | 2019-031476 | A | 2/2019 |
| JP | 2020-090482 | A | 6/2020 |
| RU | 2004135392 | A | 6/2005 |
| TW | 201524952 | A | 7/2015 |
| TW | 201524959 | A | 7/2015 |
| WO | 90/05719 | A1 | 5/1990 |
| WO | 92/05179 | A1 | 4/1992 |
| WO | 92/20642 | A1 | 11/1992 |
| WO | 93/11130 | A1 | 6/1993 |
| WO | 94/02136 | A1 | 2/1994 |
| WO | 94/02485 | A1 | 2/1994 |
| WO | 94/09010 | A1 | 4/1994 |
| WO | 95/09847 | A1 | 4/1995 |
| WO | 95/14023 | A1 | 5/1995 |
| WO | 95/16691 | A1 | 6/1995 |
| WO | 95/19774 | A1 | 7/1995 |
| WO | 95/19970 | A1 | 7/1995 |
| WO | 96/27583 | A1 | 9/1996 |
| WO | 96/30347 | A1 | 10/1996 |
| WO | 96/31510 | A1 | 10/1996 |
| WO | 96/33172 | A1 | 10/1996 |

(56) References Cited

FOREIGN PATENT DOCUMENTS

| | | | |
|---|---|---|---|
| WO | 96/33980 | A1 | 10/1996 |
| WO | 96/41807 | A1 | 12/1996 |
| WO | 97/02266 | A1 | 1/1997 |
| WO | 97/13771 | A1 | 4/1997 |
| WO | 97/19065 | A1 | 5/1997 |
| WO | 97/27199 | A1 | 7/1997 |
| WO | 97/30034 | A1 | 8/1997 |
| WO | 97/30044 | A1 | 8/1997 |
| WO | 97/32880 | A1 | 9/1997 |
| WO | 97/32881 | A1 | 9/1997 |
| WO | 97/34895 | A1 | 9/1997 |
| WO | 97/38983 | A1 | 10/1997 |
| WO | 97/38994 | A1 | 10/1997 |
| WO | 97/49688 | A1 | 12/1997 |
| WO | 98/02434 | A1 | 1/1998 |
| WO | 98/02437 | A1 | 1/1998 |
| WO | 98/02438 | A1 | 1/1998 |
| WO | 98/02441 | A2 | 1/1998 |
| WO | 98/03516 | A1 | 1/1998 |
| WO | 98/06842 | A1 | 2/1998 |
| WO | 98/07697 | A1 | 2/1998 |
| WO | 98/07726 | A1 | 2/1998 |
| WO | 98/14449 | A1 | 4/1998 |
| WO | 98/14450 | A1 | 4/1998 |
| WO | 98/14451 | A1 | 4/1998 |
| WO | 98/17662 | A1 | 4/1998 |
| WO | 98/30566 | A1 | 7/1998 |
| WO | 98/33768 | A1 | 8/1998 |
| WO | 98/33798 | A2 | 8/1998 |
| WO | 98/34915 | A1 | 8/1998 |
| WO | 98/34918 | A1 | 8/1998 |
| WO | 99/07675 | A1 | 2/1999 |
| WO | 99/07701 | A1 | 2/1999 |
| WO | 99/20758 | A1 | 4/1999 |
| WO | 99/29667 | A1 | 6/1999 |
| WO | 99/35132 | A1 | 7/1999 |
| WO | 99/35146 | A1 | 7/1999 |
| WO | 99/40196 | A1 | 8/1999 |
| WO | 99/45009 | A1 | 9/1999 |
| WO | 99/52889 | A1 | 10/1999 |
| WO | 99/52910 | A1 | 10/1999 |
| WO | 99/61422 | A1 | 12/1999 |
| WO | 00/02871 | A1 | 1/2000 |
| WO | 00/12089 | | 3/2000 |
| WO | 00/59509 | A1 | 10/2000 |
| WO | 00/74681 | A1 | 12/2000 |
| WO | 01/03720 | A2 | 1/2001 |
| WO | 01/14387 | A1 | 3/2001 |
| WO | 01/32651 | A1 | 5/2001 |
| WO | 01/37820 | A2 | 5/2001 |
| WO | 02/55501 | A2 | 7/2002 |
| WO | 02/59110 | A1 | 8/2002 |
| WO | 02/66470 | A1 | 8/2002 |
| WO | 02/68406 | A2 | 9/2002 |
| WO | 03/42132 | A1 | 5/2003 |
| WO | 2004/005279 | A2 | 1/2004 |
| WO | 2004/007458 | A1 | 1/2004 |
| WO | 2004/007481 | A2 | 1/2004 |
| WO | 2004/009784 | A2 | 1/2004 |
| WO | 2005/005434 | A1 | 1/2005 |
| WO | 2005/007190 | A1 | 1/2005 |
| WO | 2005/011700 | A1 | 2/2005 |
| WO | 2005/016252 | A2 | 2/2005 |
| WO | 2005/021546 | A1 | 3/2005 |
| WO | 2005/055808 | A2 | 6/2005 |
| WO | 2005/103005 | A1 | 11/2005 |
| WO | 2005/115451 | A2 | 12/2005 |
| WO | 2006/044453 | A1 | 4/2006 |
| WO | 2006/083289 | A2 | 8/2006 |
| WO | 2006/121168 | A1 | 11/2006 |
| WO | 2006/122806 | A2 | 11/2006 |
| WO | 2007/133822 | A1 | 11/2007 |
| WO | 2008/070740 | A1 | 6/2008 |
| WO | 2009/036082 | A2 | 3/2009 |
| WO | 2009/038057 | A1 | 3/2009 |
| WO | 2009/055730 | A1 | 4/2009 |
| WO | 2010/003118 | A1 | 1/2010 |
| WO | 2011/028683 | | 3/2011 |
| WO | 2011/051726 | A2 | 5/2011 |
| WO | 2011/090754 | A1 | 7/2011 |
| WO | 2012/142498 | A2 | 10/2012 |
| WO | 2013/039954 | A1 | 3/2013 |
| WO | 2013/155223 | A1 | 10/2013 |
| WO | 2014/143659 | A1 | 9/2014 |
| WO | 2014/152588 | A1 | 9/2014 |
| WO | 2015/001076 | A1 | 1/2015 |
| WO | 2015/054572 | A1 | 4/2015 |
| WO | 2015/075483 | A1 | 5/2015 |
| WO | 2016/044772 | A1 | 3/2016 |
| WO | 2016/049524 | A1 | 3/2016 |
| WO | 2016/049565 | A1 | 3/2016 |
| WO | 2016/049568 | A1 | 3/2016 |
| WO | 2016/164675 | A1 | 10/2016 |
| WO | 2016/168540 | A1 | 10/2016 |
| WO | 2017/015562 | A1 | 1/2017 |
| WO | 2017/058728 | A1 | 4/2017 |
| WO | 2017/058768 | A1 | 4/2017 |
| WO | 2017/058792 | A1 | 4/2017 |
| WO | 2017/058805 | A1 | 4/2017 |
| WO | 2017/058807 | A1 | 4/2017 |
| WO | 2017/058902 | A1 | 4/2017 |
| WO | 2017/058915 | A1 | 4/2017 |
| WO | 2017/087528 | A1 | 5/2017 |
| WO | 2017/100546 | A1 | 6/2017 |
| WO | 2017/172979 | A1 | 10/2017 |
| WO | 2017/201161 | A1 | 11/2017 |
| WO | 2018/064510 | A1 | 4/2018 |
| WO | 2018/068017 | A1 | 4/2018 |
| WO | 2018119183 | A2 | 6/2018 |
| WO | 2018/140598 | A1 | 8/2018 |
| WO | 2018/218069 | A1 | 11/2018 |
| WO | 2018217651 | A1 | 11/2018 |
| WO | 2019/051291 | A1 | 3/2019 |
| WO | 2019/213516 | A1 | 11/2019 |
| WO | 2019/213526 | A1 | 11/2019 |
| WO | 2019/217691 | A1 | 11/2019 |
| WO | 2019/232419 | A1 | 12/2019 |
| WO | 2019/241157 | A1 | 12/2019 |
| WO | 2019/243533 | A1 | 12/2019 |
| WO | 2019/243535 | A1 | 12/2019 |
| WO | 2020/050890 | A2 | 3/2020 |
| WO | 2020/106640 | A1 | 5/2020 |
| WO | 2020102730 | A1 | 5/2020 |
| WO | 2020/232130 | A1 | 11/2020 |
| WO | 2020/236947 | A1 | 11/2020 |
| WO | 2020/236948 | A1 | 11/2020 |
| WO | 2021/081212 | A1 | 4/2021 |
| WO | 2021097207 | A1 | 5/2021 |
| WO | 2021097212 | A1 | 5/2021 |
| WO | 2021/126816 | A1 | 6/2021 |
| WO | 2022/076623 | A1 | 4/2022 |
| WO | 2022/109242 | A1 | 5/2022 |
| WO | 2023/172858 | A1 | 9/2023 |

OTHER PUBLICATIONS

"A Phase 1, Study Evaluating the Safety, Tolerability, PK, and Efficacy of AMG 510 in Subjects With Solid Tumors With a S Mutation." NCT03600883, comparison of version submitted Oct. 29, 2018 and Oct. 9, 2019 (update posted Oct. 10, 2019), for fullhistory of change see https://clinicaltrials.gov/ct2/history/NCT03600883 (last accessed Nov. 11, 2020), pp. 1-22.

"Acute Leukemia," The Merck Manual (Online Edition), pp. 1-6 (2013).

"KRASG12C Inhibitor," Mirati Therapeutics, retrieved on Nov. 27, 2018, from https://www.mirati.com/mrtx849/, 5 pages.

4-methyl-2-(1-methylethyl)-3-Pyridinamine, STN Registry, Cas RN 1698293-93-4, STN entry date May 5, 2015 (May 5, 2015).

Ahmadian, et al., "Guanosine triphosphatase stimulation of oncogenic Ras mutants," PNAS, 96: 7065-7070, 1999.

(56) References Cited

OTHER PUBLICATIONS

Airoldi, et al., "Glucose-Derived Ras Pathway Inhibitors: Evidence of Ras-Ligand Binding and Ras-GEF (Cdc25) Interaction Inhibition," ChemBioChem, 8: 1376-1379 (2007).
AMG-510; CS-0081316; Source: AbaChemScene (CS-0081316); Deposit Date: May 13, 2019 Available Date: May 13, 2019; SID: 384060804[CID: 137278711] (available athttps://pubchem.ncbi.nlm.nih.gov/substance/384060804/).
AMG-510; HY-114277; Source: MedChemexpress MCE (HY-114277); Deposit Date: May 13, 2019 Available Date: May 13, 2019; SID: 384060569[CID: 137278711] (available at https://pubchem.ncbi.nlm.nih.gov/substance/384060569).
Amgen Press Release, "Amgen Announces New Clinical Data Evaluating Novel Investigational KRAS(G12C) Inhibitor In Larger Patient Group At WCLC 2019," Sep. 8, 2019 (available at https://wwwext.amgen.com/newsroom/press-releases/2019/09/amgen-announces-new-clinical-data-evaluating-novel-investigational-krasg12c-inhibitor-in-larger-patient-group-at-wclc-2019, last accessed Jun. 16, 2023), pp. 1-7.
ATTC "Organism: Mus musculus (B cell); Mus musculus (myeloma), mouse (B cell); mouse (myeloma)," Accession No. HB-8508, retrieved from https://www.atcc.org/-/media/0DF7351153724BD6A3E7D78D5BA2F933.ashx, on Nov. 29, 2018.
Barnett, et al., "Identification and characterization of pleckstrin-holomogy-domain-dependent and isoenzyme specific Akt inhibitors," Biochem. J, 385 (2): 399-408 (2005).
Beaver, et al., Axial Chirality in the Sotorasib Drug Substance, Part 2: Leveraging a high-Temperature Thermal Racemization to Recyle the Classical Resolution Waste System, Org Process res. Dev. 26: 2636-2645 (2022).
Bhatia, et al., "A Review on Bioisosterism: A Rational Approach for Drug Design and Molecular Modification," Pharmacologyonline, 1:272-299 (2011).
Biernacka, et al., "The potential utility of re-mining results of somatic mutation testing: KRAS status in lung adenocarcinoma" in Cancer Genet;209:195-8 (2016).
Bull, et al., "Isoquino[2,1-c][1,3,2] Benzodiazaphosphorine Derivatives: New Potential Agents for Cancer Chemotherapy," Phosphorus, Sulfur, and Silicon, 162:231-243 (2000).
Campillo, et al., "Novel Bronchodilators: Synthesis, Transamination Reactions, and Pharmacology of a Series of Pyrazino[2,3-c][I,2,6]thiadiazine 2,2-Dioxides," J Med Chem., 43: 4219-4227 (2000).
Canon, et al., "The clinical KRAS(G12C) inhibitor AMG 510 drives anti-tumour immunity," Nature, 575(7781): 217-223 (2019).
Cee, et al., "Discovery of AMG 510, a first-in-humancovalent inhibitor of KRASG12c for the treatment of solid tumors," Abstract and Presentation, ACS Spring Meeting, Orlando, FL, USA, Mar. 31-Apr. 4, 2019.
Clarke, et al., "Dissecting mechanisms of resistance to targeted drug combination therapy in human colorectal cancer" in Oncogene 38:5076-90 (2019).
Cohen, "The development and therapeutic potential of protein kinase inhibitors," Current Opinion in Chemical Biolof! V, 3:459-465 (I 999).
Cowen Slide deck—Warp Drive Bio, slides 1-32, "Corporate Overview Exploiting the Molecules and Mechanisms of Nature to Create Transformative Medicines" http://www.warpdrivebio.com/news/cowen%/o202016.pdf (last visited Apr. 2016).
Cox, et al.,. "Drugging the undruggable RAS: mission possible?" in Nat Rev Drug Discov 13:828-51 M(2014).
Dai et al., "Synthesis of Substituted Pyridines via Formal (3+3) Cycloaddition of Enamines with Unsaturated Aldehydes and Ketones," J. Org. Chem., 87:8437-44 (2022).
Dasmahapatra et al. "In vitro combination treatment with perifosine and UCN-01 demonstrates synergism against prostate (PC-3) and lung (A549) epithelial adenocarcinoma cell lines," Clin. Cancer Res., vol. 10(15), pp. 5242-5252 (2004).
Database Registry [Online], Chemical Abstracts Service, Columbus, Ohio, US; Jul. 31, 2017 (Jul. 31, 2017), XP002801805, retrieved from STN Database accession No. 2105944-09-8.
Del Re , et al., "Implications of KRAS mutations in acquired resistance to treatment in NSCLC" in Oncotarget 9:6630-43 (2018).
Dermer, et al., "Another Anniversary for the War on Cancer," Bio/Technology, 12: 320 (1994).
Douelle, et al., "Highly Diastereoselective Synthesis of vicinal Quaternary and Tertiary Stereocenters Using the lodo-aldol Cyclization," Org. Lett., 9 (10): 1931-1934 (2007).
Erkkila, et al., "Mild Organocatalytic a-Methylenation of Aldehydes," J Org. Chem., 71 (6), 2538-2541 (2006).
Extended European Search Report for European Patent Application No. 19208193.2, dated Jun. 3, 2020, pp. 1-8.
Fakih, et al., "Phase 1 study evaluating the safety, tolerability, pharmacokinetics (PK), and efficacy of AMG 510, a novel small molecule KRASG12C inhibitor, in advanced solid tumors," Journal of Clinical Oncology, 37(15 suppl) (May 20, 2019) 3003, published online May 26, 2019.
Fiala, et al.,. "G12V and G12A KRAS mutations are associated with poor outcome in patients with metastatic colorectal cancer treated with bevacizumab" in Tumour Biol 37:6823-30 (2016).
Final Office Action for U.S. Appl. No. 15/984,855, mailed Mar. 28, 2019, 7 pages.
Final Office Action for U.S. Appl. No. 16/436,647, mailed Mar. 24, 2021, 7 pages.
Final Office Action for U.S. Appl. No. 16/661,907, mailed Mar. 27, 2020, 29 pages.
Freshney, et al., Culture of Animal Cells, A Manual of Basic Technique, Alan R. Liss, Inc, New York, p. 4 (1983).
Gentile, et al., "Discovery and Structural Investigation of Novel Binders to the Ras Switch II Pocket," NCI Initiative Symposium Poster (2015).
Gills and Dennis, "The development of phosphatidylinositol ether lipid analogues as inhibitors of the serine/threonine kinase, Akt," Expert. Opin. Investig. Drugs, 13: 787-797 (2004).
Goldberg, et al., "Role of PD-1 and its ligand, B7-H1, in early fate decisions of CD8 T cells," Blood, 110(1):186-192 (2007).
Goldstein et al., "Biological efficacy of a chimeric antibody to the epidermal growth factor receptor in a human tumor xenograft model," Clin Cancer Res, vol. 1(11), pp. 1311-1318 (1995).
Golub, et al., "Molecular Classification of Cancer: Class Discovery and Class Prediction by Gene Expression Monitoring," Science, 286: 531-537(1999).
Govindan et al., "OA01.06 Safety, Efficacy, and Pharmacokinetics of AMG 510, a Novel KRASG2C Inhibitor, in Patients with Non-Small Cell Lung Cancer," J. Thorac. Oncol., 14(11, Supplement 1):S1125-1126 (Nov. 2019).
Govindan, et al., "Phase 1 Study of AMG 510, a Novel KRAS G12C Inhibitor, in Advanced Solid Tumors with KRAS p.G12C Mutation," Abstract, ESMO Congress, Barcelona, Spain, Sep. 27-Oct. 1, 2019.
Govindan, et al., "Phase 1 Study of Safety, Tolerability, Pharmacokinetics, and Efficacy of AMG510, a Novel KRASG12C Inhibitor, in Non-Small Cell Lung Cancer," Abstract and Presentation, World Conference on Lung Cancer (WCLC), Barcelona, Spain, Sep. 7-10, 2019.
Govindan, et al., "Safety, Efficacy, and Pharmacokinetics of AMG 510, a Novel KRASG12C Inhibitor, in Patients with Non-Small Cell Lung Cancer," Abstract and Presentation, North American Conference on Lung Cancer (NACLC), Chicago, IL, USA, Oct. 10-12, 2019.
Gura, "Cancer Models: Systems for Identifying New Drugs Are Often Faulty," Science, 278(5340): 1041-1042 (1997).
Halford, "Amgen unveils its Kras covalent inhibitor AMG 510," Chemical & Engineering News 97(14) :4 (2019).
Hallin, et al., "The KRASG12c Inhibitor MRTX849 Provides Insight toward Therapeutic Susceptibility of KRAS-Mutant Cancers in Mouse Models and Patients,"Cancer Discov., 10: 54-71 (2020).
Hansen, et al., "Abstract 686: Drugging an undruggable pocket: the biochemical mechanism of covalent KRASG12c inhibitors," Proceedings of the American Association for Cancer Research Annual

(56) References Cited

OTHER PUBLICATIONS

Meeting 2018; Apr. 14-18, 2018; Chicago, IL; AACR; CancerRes., 78(13 Suppl): Abstract 686 (2018).
Hichri, et al., "A Convenient Synthesis of 1,3,2-Benzodiazaphophorine-2-Oxide," Phosphorus, Sulfur, and Silicon, 190: 29-35 (2015).
National Cancer Institute identifier: NSC 154020, retrieved on Nov. 29, 2018, from https://cactus.nci .nih.gov/ncidb2.2/.
NCBI Reference Sequence, "GTPase KRas isoform a [*Homo sapiens*]," GenBank Accession No. NM_203524. I, Retrieved on Nov. 29, 2018 fromhttps://www.ncbi.nlm.nih.gov/protein/I57I8763?sat=4&satkey=234448549, 4 pages.
Neumann, et al.,. "Frequency and type of KRAS mutations in routine diagnostic analysis of metastatic colorectal cancer" in Pathol Res Pract 205:858-62 (2009).
Non-Final Office Action (Corrected) for U.S. Appl. No. 16/125,359, mailed Apr. 8, 2019, 13 pages.
Non-Final Office Action for U.S. Appl. No. 15/849,905, mailed Mar. 20, 2019, 18 pages.
Non-Final Office Action for U.S. Appl. No. 15/984,855, mailed Sep. 27, 2018, 25 pages.
Non-Final Office Action for U.S. Appl. No. 16/125,359, mailed Apr. 5, 2019, 13 pages.
Non-Final Office Action for U.S. Appl. No. 16/402,538, mailed Oct. 30, 2019, 12 pages.
Non-Final Office Action for U.S. Appl. No. 16/402,589, mailed Mar. 6, 2020, 17 pages.
Non-Final Office Action for U.S. Appl. No. 16/407,889, mailed Jul. 1, 2020, 6 pages.
Non-Final Office Action for U.S. Appl. No. 16/428,163, mailed Sep. 15, 2020, 6 pages.
Non-Final Office Action for U.S. Appl. No. 16/436,647, mailed Aug. 7, 2020, 19 pages.
Non-Final Office Action for U.S. Appl. No. 16/438,349, mailed Dec. 13, 2019, 15 pages.
Non-Final Office Action for U.S. Appl. No. 16/661,907, mailed Nov. 18, 2019, 20 pages.
Non-Final Office Action for U.S. Appl. No. 16/675,121, mailed Feb. 2, 2021, 10pages.
Non-Final Office Action for U.S. Appl. No. 16/817,109, mailed Mar. 3, 2021, 12 pages.
Non-Final Office Action for U.S. Appl. No. 17/031,607, mailed Mar. 31, 2023, 7 pages.
Non-Final Office Action for U.S. Appl. No. 17/689,741, mailed Apr. 1, 2025, 7 pages.
Noriyuki, "API Form Screening and Selection at the Drug Discovery Stage", Pharmstage, vol. 6, No. 10, Jan. 15, 2007, pp. 20-25 (incl. English translation).
Notice of Allowance mailed Jan. 14, 2021 for U.S. Appl. No. 16/402,589, 5 pages.
Notice of Allowance mailed Jul. 24, 2020 for U.S. Appl. No. 16/402,538, 8 pages.
Notice of Allowance mailed Jun. 30, 2021 for U.S. Appl. No. 16/438,349, pp. 1-9.
Notice of Allowance mailed Sep. 16, 2020 for U.S. Appl. No. 16/402,589 5 pages.
Notice of Allowance mailed Sep. 9, 2020 for U.S. Appl. No. 16/438,349, 9 pages.
Notice of Allowance, mailed Feb. 18, 2021, for U.S. Appl. No. 16/687,546, 9 pages.
Notice of Allowance, mailed Jan. 26, 2021, for U.S. Appl. No. 16/438,349, 9 pages.
Notice of Allowance, mailed Jan. 27, 2021, for U.S. Appl. No. 16/428,163, 9 oages.
Notice of Allowance, mailed Mar. 30, 2021, for U.S. Appl. No. 16/402,538, 8 pages.
Notice of Allowance, mailed Oct. 20, 2021, for U.S. Appl. No. 16/438,349, 9 pages.
Notice of Allowance, mailed Apr. 19, 2021, for U.S. Appl. No. 16/428,163, 9 pages.
Notice of Allowance, mailed Aug. 13, 2019, for U.S. Appl. No. 15/984,855, 5 pages.
Notice of Allowance, mailed Dec. 21, 2020, for U.S. Appl. No. 16/407,889, 5 pages.
Notice of Allowance, mailed Oct. 3, 2023, for U.S. Appl. No. 17/031,607, 7 pages.
Notice of Allowance, mailed Sep. 22, 2021, for U.S. Appl. No. 16/878,824, 8 pages.
Notice of Allowance, mailed Sep. 9, 2021, for U.S. Appl. No. 16/675,121, 7 pages.
Ostrem JM, et al. K-Ras(G12C) inhibitors allosterically control GTP affinity and effector interactions. Nature. 2013;503(7477):548-551.
Ostrem, et al., "Development of mutant-specific small molecule inhibitors ofK-Ras,"Poster, AACR 104th Annual Meeting 2013; Apr. 6-10, 2013; Washington, D.C. (2013).
Ostrem, et al., "Direct small molecule inhibitors of KRAS: from structural insights to mechanism-based design" in Nat Rev Drug Discov 15:771-85 (2016).
Ouerhani, et al.,. "The mutational spectrum of HRAS, KRAS, NRAS and FGFR3 genes in bladder cancer" in Cancer Biomark 2011-2012;10:259-66 (2012).
Paez et al., "EGFR Mutations In Lung Cancer Correlation With Clinical Response To Gefitinib Therapy," Science, vol. 304(5676), pp. 1497-1500 (2004).
Palmioli, et al., "First experimental identification of Ras-inhibitor binding interface using a water-soluble Ras ligand," Bioorz. Med Chem. Lett., 19: 4217-4222 (2009).
Parsons, et al., Axial Chirality in the Sotorasib Drug Substance, Part 1: Development of a Classical Resolution to Prepare an Atropisomerically Pure Sotorasib Intermediate, Org. Process res. Dev. 26: 2629-2635 (2022).
Patricelli MP, et al. Selective Inhibition of Oncogenic KRAS Output with Small Molecules Targeting the Inactive State. Cancer Discov. 2016;6(3):316-329.
Pearce, et al., "Failure modes in anticancer drug discovery and development," Cancer Drug Design and Discovery, Edited by Stephen Neidle, Chapter 18, pp. 424-443 5 (2008).
Peri, et al., "Design, Synthesis and Biological Evaluation of Sugar-Derived Ras Inhibitors," ChemBioChem, 6: 1839-1848 (2005).
Peri, et al., "Sugar-Derived Ras Inhibitors: Group Epitope Mapping by NMR Spectroscopy and Biological Evaluation," Eur. J Org. Chem., 16: 3707-3720 (2006).
Peters, et al., "Selective inhibition of K-Ras G12C through allosteric control of GTP affinity and effector interactions," EORTC Poster (2013).
PubChem CID 108190520, 2-isopropyl-4-methylpyridin-3-amine, available at https://pubchem.ncbi.nlm.nih.gov/compound/108190520 (last accessed Aug. 30, 2021).
Remington's Pharmaceutical Sciences, 1435-1712 (18th ed., Mack Publishing Co, Easton, Pennsylvania, 1990 (Table of Contents Only).
Restriction Requirement, mailed Apr. 14, 2022, for U.S. Appl. No. 17/031,607, 5 pages.
Hichri, et al., CAPLUS Abstract, 162:245378 (2015).
Hirayama, "Handbook for Making Crystal of Organic Compound,—Principles and Know-how—", Maruzen Co., Ltd., Jul. 25, 2008, pp. 57-84 (incl. English translation).
Hocker, et al., "Andrographolide derivatives inhibit guanine nucleotide exchange and abrogate oncogenic Ras function," PNAS, 110(25): 10201-10206 (2013).
Hong, et al., "KRASG12C Inhibition with Sotorasib in Advanced Solid Tumors," N. Engl. Med., 383:1207-1217 (2020).
Huang, et al., "Epidermal Growth Factor Receptor Blockade with C225 Modulates Proliferation, Apoptosis, and Radiosensitivity in Squamous Cell Carcinomas of the Head and Neck," Cancer Res., 59(8): 1935-1940 (1999).
Intention to grant received for European Patent Application No. 23174717.1, mailed on Nov. 13, 2025, 6 pages.
International Search Report for PCT/US2017/067801, mailed Jul. 25, 2018, 6 pages.
International Search Report for PCT/US2018/033714, mailed Jul. 17, 2018, 3 pages.

(56) References Cited

OTHER PUBLICATIONS

International Search Report for PCT/US2018/050044, mailed Oct. 30, 2018, 7 pages.
International Search Report for PCT/US2019/030593, mailed Aug. 6, 2019, 4 pages.
International Search Report for PCT/US2019/030606, mailed Jul. 23, 2019, 5 pages.
International Search Report for PCT/US2019/031535, mailed Jul. 25, 2019, 7 pages.
International Search Report for PCT/US2019/034974, mailed Aug. 9, 2019, 5 pages.
International Search Report for PCT/US2019/036397, mailed Aug. 26, 2019, 5 pages.
International Search Report for PCT/US2019/036626, mailed Jun. 2, 2020, 5 pages.
International Search Report for PCT/US2019/061815, mailed Mar. 5, 2020, 6 pages.
International Search Report for PCT/US2019/062051, mailed Mar. 2, 2020, 3 pages.
International Search Report for PCT/US2019/62064, mailed Oct. 29, 2020, 9 pages.
International Search Report for PCT/US2020/032686, mailed Aug. 14, 2020, 4 pages.
International Search Report for PCT/US2020/033832, mailed Jul. 8, 2020, 4 pages.
International Search Report for PCT/US2020/060415, mailed Feb. 3, 2021, 5 pages.
International Search Report for PCT/US2020/065050, mailed Mar. 29, 2021, 7 pages.
International Search Report for PCT/US2020/033831, mailed Jul. 9, 2020, 6 pages.
Janes, et al., "Targeting KRAS Mutant Cancers with a Covalent G12C-Specific Inhibitor," Cell, 172: 578-589 (2018).
Jarvis, "Notorious KRAS: Taking down cancer researchers' biggest foe," Chemical & Engineering News, 97(37), 9 pages (2019).
Jin, et al., "Inhibition of AKT survival pathway by a small molecule inhibitor in human endometrial cancer cells," Br. J Cancer, 91: 1808-1812 (2004).
Johnson et al., "Relationships between drug activity in NCI preclinical in vitro and in vivo models and early clinical trials," British Journal of Cancer, 84(10): 1424-1431 (2001).
Kargbo RB. "Inhibitors of G12C mutant Ras proteins for the treatment of cancers" in ACS Med Chem Lett 10:10-1 (2018).
Kojima, "Aiming to Improve the Efficiency of Crystallization Selection in Drug Development", Pharmaceutics, Sep. 1, 2008, vol. 68, No. 5, pp. 344-349 (incl. English translation).
Lanman BA, et al. Abstract 4455: Discovery of AMG 510, a first-in-human covalent inhibitor of KRASG12C for the treatment of solid tumors. Presentation, American Association for Cancer Research (AACR) Annual Meeting, Atlanta, GA, USA, Mar. 29-Apr. 3, 2019, pp. 1-18.
Lanman, et al., "Discovery of a Covalent Inhibitor of KRASG12C (AMG 510) for the Treatment of Solid Tumors," J. Med Chem., 63: 52-65 (2020).
Lanman, et al., Addressing Atropisomerism in the Development of Sotorasib, a Covalent Inhibitor of KRAS G12C: Structural, Analytical and Synthetic Considerations, ACS Publications 55: 289-2903 (2022).
Li, et al., "Targeting Protein-Protein Interaction with Covalent Small-Molecule Inhibitors," Current Topics in Medicinal Chemistry, 19(21): 1872-1876 (2019).
Lievre , et al.,. "KRAS mutation status is predictive of response to cetuximab therapy in colorectal cancer" in Cancer Res 66:3992-5 (2006).
Lim, et al., "Therapeutic Targeting of Oncogenic K-Ras by a Covalent Catalytic Site Inhibitor," An?ew. Chem. Int. Ed, 53: 199-204 (2014).
Lipford, et al., "Pre-Clinical Development of AMG 510: The First Inhibitor of KRASG12C in Clinical Testing," Presentation, American Association for Cancer Research (AACR) Annual Meeting, Atlanta, GA, USA, Mar. 29-Apr. 3, 2019.
Lito , et al., "Allele-specific inhibitors inactivate mutant KRAS G12C by a trapping mechanism" in Science 351:604-8 (2016).
Liu, Y., "Session SY28—Transformative Small Molecule Therapies—Targeting KRAS mutant cancers with a covalent G12C—specific inhibitor," Presentation on Apr. 4, 2017,AACR Annual Meeting Presentation, Apr. 1-5, 2017, Washington, D.C. (2017).
Lopez, et al., "Optimization of quinazolinone-based covalent inhibitors of KRASG12C in the discovery of AMG 510," Abstract and Poster, ACS Fall Meeting, San Diego, CA, USA, Aug. 25-29, 2019.
Lu, et al., "KRAS G12C Drug Development: Discrimination between Switch II Pocket Configurations Using Hydrogen/Deuterium-Exchange Mass Spectrometry," Structure, 25: 1-7 (2017).
Massarelli , et al., "KRAS mutation is an important predictor of resistance to therapy with epidermal growth factor receptor tyrosine kinase inhibitors in non-small-cell lung cancer" in Clin Cancer Res 13:2890-6 (2007).
Maurer, et al., "Small-molecule ligands bind to a distinct pocket in Rad and inhibit SOS-mediated nucleotide exchange activity," PNAS, 109(14): 5299-5304 (2012).
Mccormick F. "K-Ras protein as a drug target" in J Mal Med (Berl) 2016;94:253-8; Jones RP, Sutton PA, Evans JP, et al. "Specific mutations in KRAS codon 12 are associated with worse overall survival in patients with advanced and recurrent colorectal cancer" in Br J Cancer 116:923-9 (2017).
Mcgregor, et al., "Expanding the Scope of Electrophiles Capable of Targeting K-Ras Oncogenes," ACS Bio. Chem., 56: 3179-3183 (2017).
Meanwell, "Synopsis of Some Recent Tactical Application ofBioisosteres in Drug Design," J Med Chem. 54:2529-2591 (2011).
Mirati Therapeutics, "Corporate Presentation Nov. 2017," Slides 1-41 (2017).
Modjtahedi, et al., "The human EGF receptor as a target for cancer therapy: six new rat mAbs AGainst the receptor on the breast carcinoma MDA-MB 468," Br. J Cancer, 67(2): 247-253 (1993).
Morrissey et al., "Immunotherapy and Novel Combinations in Oncology: Current Landscape, Challenges, and Opportunities," Clin. Trans. Sci., 9(2):89-104 (2016).
Murray et al., "Kinetic and Mechanistic Investigations to Enable a Key Suzuki Coupling for Sotorasib Manufacture_What a Difference a Base Makes," Org. Proc. Res. Dev., 27(1):198-205 (2023).
Nadal E, et al., "KRAS-G12C mutation is associated with poor outcome in surgically resected lung adenocarcinoma" in J Thorac Oncol 9:1513-22 (2014).
Restriction Requirement, mailed Feb. 24, 2025 for U.S. Appl. No. 18/987,607, 7 pages.
Restriction Requirement, mailed May 7, 2025, for U.S. Appl. No. 18/987,568, 5 pages.
Restriction Requirement, mailed Sep. 29, 2024 for U.S. Appl. No. 17/689,741, 9 pages.
Rex et al., "KRAS-AACR 2018," Amgen Collection of Information published at Proceedings of the American Association for Cancer Research Annual Meeting 2018; Apr. 14-18, 2018; Chicago, IL; AACR; slides 1-24 (2018).
Rex K, et al. Abstract 3090: In vivo characterization of AMG 510—a potent and selective KRASG12C covalent small molecule inhibitor in preclinical KRASG12C cancer models. Proceedings of the American Association for Cancer Research Annual Meeting 2019; Mar. 29-Apr. 3, 2019; Atlanta, GA, USA, AACR, Cancer Res. 2019;79(13 Suppl): Abstract nr 3090, pp. 1-4.
Saiki, et al., "Abstract 4484: Discovery and in vitro characterization of AMG 510-a potent and selective covalent small-molecule inhibitor ofKRASG12c," Presentation, American Association for Cancer Research (AACR) Annual Meeting, Atlanta, GA, USA, Mar. 29-Apr. 3, 2019.
Sarkar et al., "Indole-3-carbinol and prostate cancer," J Nutr., vol. 134(12 Suppl), pp. 3493S-3498S (2004).
Shibata et al., "A Convenient Synthesis of 3-Cyano-2-methylpyridines under Ultrasonic Irradiation," Bull. Chem. Soc. Jpn., 61:2199-2200 (1988).

(56) References Cited

OTHER PUBLICATIONS

Shima, et al., "In silica discovery of small-molecule Ras inhibitors that displayantitumor activity by blocking the Ras-effector interaction," PNAS, 110(20): 8182-8187 (2013).
Simanshu DK, et al. RAS Proteins and Their Regulators in Human Disease. Cell. 2017;170(1):17-33.
Simone, "Part XIV Oncology: Introduction," Cecil Textbook of Medicine, 20th Edition, 1:1004-1010 (1996).
Singh, et al., "Improving Prospects for Targeting RAS," J Cline. Oncl, 33(31): 3650-3660 (2015).
Stanetty et al., "Synthesis of Aza Analogs of the Herbicide Sindone B," Monatshefte Fuer Chemie, 130:441-450 (1999).
Statsyuk, "Let K-Ras activate its own inhibitor," Nature Structural & Molecular Biolof!V, 25:435-439 (2018).
Sun, et al., "Discovery of Small Molecules that Bind to K-Ras and Inhibit Sos-Mediated Activation," Angew. Chem. Int. Ed., 51: 6140-6143 (2012).
Suzawa, et al., "Activation of KRAS mediates resistance to targeted therapy in MET exon 14-mutant non-small cell lung cancer" in Clin Cancer Res 2019;25:1248-60 (2019).
Synoradski, et al., Tartaric Acid and Its o-Acyl derivatives. Part 2. Applications of Tartaric Acid and of O-Acyl Tartaric Acids and anhydrides. Resolution of Racemates, Organic Prep. Proc. Int. 40(2): 163-200 (2008).
Taveras, et al., "Ras Oncoprotein Inhibitors: The Discovery of Potent, Ras Nucleotide Exchange Inhibitors and the Structural Determination of a Drug-Protein Complex," Biorg. Med Chem. Lett.,, 5(1): 125-133 (1997).
Teramoto, et al., 1996, Cancer 77 (4):639-645.
The ASCO Post Staff, "AACR-NCI-EORTC: Investigational KRAS G12C Inhibitor for KRAS-Mutant Solid Tumors," The ASCO Post (2019).
Third Party Observation filed for PCT/US2020/033831, submitted Jan. 15, 2021, 2 pages.
Thompson, et al., "PD-1 Is Expressed by Tumor-Infiltrating Immune Cells and Is Associated with Poor Outcome for Patients with Renal Cell Carcinoma," Clin. Cancer Res., 13(6): 1757-1761 (2007).
Traxler, "Tyrosine kinase inhibitors in cancer treatment (Part II)," Exp. Opin. Ther. Patents, 8(12): 1599-1625 (1998).
U.S. Appl. No. 60/528,340, filed Dec. 9, 2003.
Wang, et al., "Ras inhibition via direct Ras binding—is there a path forward?," Bioorg. Med Chem. Lett., 22: 5766-5776 (2012).
Written Opinion for PCT/US2017/067801, mailed Jul. 25, 2018, 10 pages.
Written Opinion for PCT/US2018/033714, mailed Jul. 17, 2018, 5 pages.
Written Opinion for PCT/US2018/050044, mailed Oct. 30, 2018, 7 pages.
Written Opinion for PCT/US2019/030593, mailed Aug. 6, 2019, 5 pages.
Written Opinion for PCT/US2019/030606, mailed Jul. 23, 2019, 6 pages.
Written Opinion for PCT/US2019/031535, mailed Jul. 25, 2019, 7 pages.
Written Opinion for PCT/US2019/034974, mailed Aug. 9, 2019, 5 pages.
Written Opinion for PCT/US2019/036397, mailed Aug. 26, 2019, 5 pages.
Written Opinion for PCT/US2019/036626, mailed Jun. 2, 2020, 12 pages.
Written Opinion for PCT/US2019/061815, mailed Mar. 5, 2020, 4 pages.
Written Opinion for PCT/US2019/062051, mailed Mar. 2, 2020, 5 pages.
Written Opinion for PCT/US2019/62064, mailed Oct. 29, 2020, 13 pages.
Written Opinion for PCT/US2020/032686, mailed Aug. 14, 2020, pp. 1-6.
Written Opinion for PCT/US2020/033831, mailed Jul. 9, 2020, 7 pages.
Written Opinion for PCT/US2020/033832, mailed Jul. 8, 2020, 6 pages.
Written Opinion for PCT/US2020/060415, mailed Feb. 3, 2021, 9 pages.
Written Opinion for PCT/US2020/065050, mailed Mar. 29, 2021, 8 pages.
Xing, et al., An Improved Efficient Process for the Production of highly Pure Dexmethylphenidate Hydrochloride, J Heterocylic Chem., 54:1298-1303 (2017).
Xiong, et al., "Covalent Guanosine Mimetic Inhibitors of G12C KRAS," A CS Med. Chem. Lett., 8: 61-66 (2017).
Yan et al., "Pharmacogenics and pharmacogenomics in oncology therapeutic antibody development," BioTechniques, vol. 39, pp. 565-568 (2005).
Yang et al., "Akt/Protein Kinase B Signaling Inhibitor-2, a Selective Small Molecule Inhibitor of Akt Signaling with Antitumor Activity in Cancer Cells Overexpressing Akt", Cancer Res., vol. 64 (13), pp. 4394-4399 (2004).
Yang et al., "Eradication of established tumors by a fully human monoclonal antibody to the epidermal growth factor receptor without concomitant chemotherapy," Cancer Res., vol. 59, pp. 1236-1243 (1999).
Zeng, et al., "Potent and Selective Covalent Quinazoline Inhibitors of KRAS G12C," Cell Chemical Biology, 24: 1-12 (2017).
Zhang et al., "Development of a Commercial Manufacturing Process for Sotorasib, a First-in-Class KRASG12C Inhibitor," Organic Process Research and Development, vol. 26, pp. 3115-3125 (2022).
Zimmerman, et al., "Small molecule inhibition of the KRAS-PDE8 interactionimpairs oncogenic KRAS signaling," Nature, I-5 (2017).
Xing et al., "Fundamentals of Organic Chemistry", 1st Edition, Higher Education Press, pp. 175-176(1965).
Patel et al., "Thermal racemization of biaryl atropisomers", Tetrahedron: Asymmetry, vol. 28(11), pp. 1-5(2017).

* cited by examiner

PROCESS FOR RACEMIZING AND ISOLATING ATROPISOMERS OF 7-CHLORO-6-FLUORO-1-(2-ISOPROPYL-4-METHYLPYRIDIN-3-YL)PYRIDO [2,3-D]PYRIMIDINE-2,4(1H,3H)-DIONE

CROSS-REFERENCE TO RELATED APPLICATIONS

This application is a national stage application under 35 U.S.C. § 371 of International Application No. PCT/US2021/053859, having an international filing date of Oct. 6, 2021, claiming the benefit of U.S. Provisional Patent Application No. 63/088,848, filed Oct. 7, 2020, and U.S. Provisional Patent Application No. 63/162,278, filed Mar. 17, 2021, each of which is incorporated herein by reference in its entirety.

BACKGROUND

KIRSTEN RAT SARCOMA VIRAL ONCOGENE homologue (KRAS) is the most frequently mutated oncogene in human cancers and encodes a guanosine triphosphatase (GTPase) that cycles between active guanosine triphosphate (GTP)-bound and inactive guanosine diphosphate (GDP)-bound states to regulate signal transduction. See, for example, Simanshu D K, Nissley D V, McCormick F. "RAS proteins and their regulators in human disease" in Cell 2017; 170:17-33.

KRAS mutations are often associated with resistance to targeted therapies and poor outcomes in patients with cancer, yet no selective KRAS inhibitor has been approved despite more than three decades of scientific effort until very recently. See, for example, Nadal E, Chen G, Prensner J R, et al. "KRAS-G12C mutation is associated with poor outcome in surgically resected lung adenocarcinoma" in *J Thorac Oncol* 2014; 9:1513-22; Massarelli E, Varella-Garcia M, Tang X, et al. "KRAS mutation is an important predictor of resistance to therapy with epidermal growth factor receptor tyrosine kinase inhibitors in non-small-cell lung cancer" in *Clin Cancer Res* 2007; 13:2890-6; Fiala 0, Buchler T, Mohelnikova-Duchonova B, et al. "G12V and G12A KRAS mutations are associated with poor outcome in patients with metastatic colorectal cancer treated with bevacizumab" in *Tumour Biol* 2016; 37:6823-30; Lievre A, Bachet J-B, Le Corre D, et al. "KRAS mutation status is predictive of response to cetuximab therapy in colorectal cancer" in *Cancer Res* 2006; 66:3992-5; McCormick F. "K-Ras protein as a drug target" in *J Mol Med* (Berl) 2016; 94:253-8; Jones R P, Sutton P A, Evans J P, et al. "Specific mutations in KRAS codon 12 are associated with worse overall survival in patients with advanced and recurrent colorectal cancer" in *Br J Cancer* 2017; 116:923-9; Cox A D, Fesik S W, Kimmelman A C, Luo J, Der C J. "Drugging the undruggable RAS: mission possible?" in *Nat Rev Drug Discov* 2014; 13:828-51; Ostrem JML, Shokat K M. "Direct small molecule inhibitors of KRAS: from structural insights to mechanism-based design" in *Nat Rev Drug Discov* 2016; 15:771-85; Suzawa K, Offin M, Lu D, et al. "Activation of KRAS mediates resistance to targeted therapy in MET exon 14-mutant non-small cell lung cancer" in *Clin Cancer Res* 2019; 25:1248-60; Clarke P A, Roe T, Swabey K, et al. "Dissecting mechanisms of resistance to targeted drug combination therapy in human colorectal cancer" in Oncogene 2019; 38:5076-90; and Del Re M, Rofi E, Restante G, et al. "Implications of KRAS mutations in acquired resistance to treatment in NSCLC" in *Oncotarget* 2017; 9:6630-43.

The KRAS p.G12C mutation occurs in approximately 13% of non-small-cell lung cancers (NSCLCs) and in 1 to 3% of colorectal cancers and other solid cancers. See, for example, Cox A D, Fesik S W, Kimmelman A C, Luo J, Der C J. "Drugging the undruggable RAS: mission possible?" in *Nat Rev Drug Discov* 2014; 13:828-51; Biernacka A, Tsongalis P D, Peterson J D, et al. "The potential utility of re-mining results of somatic mutation testing: KRAS status in lung adenocarcinoma" in *Cancer Genet* 2016; 209:195-8; Neumann J, Zeindl-Eberhart E, Kirchner T, Jung A. "Frequency and type of KRAS mutations in routine diagnostic analysis of metastatic colorectal cancer" in *Pathol Res Pract* 2009; 205:858-62; and Ouerhani S, Elgaaied ABA. "The mutational spectrum of HRAS, KRAS, NRAS and FGFR3 genes in bladder cancer" in *Cancer Biomark* 2011-2012; 10:259-66.

The glycine-to-cysteine mutation at position 12 favors the active form of the KRAS protein, resulting in a predominantly GTP-bound KRAS oncoprotein and enhanced proliferation and survival in tumor cells. See, for example, Ostrem J M, Peters U, Sos M L, Wells J A, Shokat K M. "K-Ras (G12C) inhibitors allosterically control GTP affinity and effector interactions" in *Nature* 2013; 503:548-51 and Kargbo R B. "Inhibitors of G12C mutant Ras proteins for the treatment of cancers" in *ACS Med Chem Lett* 2018; 10:10-1.

The mutated cysteine resides next to a pocket (P2) of the switch II region. The P2 pocket is present only in the inactive GDP-bound conformation of KRAS and has been exploited to establish covalent inhibitors of KRAS G12C. See, for example, Ostrem J M, Peters U, Sos M L, Wells J A, Shokat K M. "K-Ras(G12C) inhibitors allosterically control GTP affinity and effector interactions" in *Nature* 2013; 503:548-51; Lito P, Solomon M, Li L-S, Hansen R, Rosen N. "Allele-specific inhibitors inactivate mutant KRAS G12C by a trapping mechanism" in Science 2016; 351:604-8; and Patricelli M P, Janes M R, Li L-S, et al. "Selective inhibition of oncogenic KRAS output with small molecules targeting the inactive state" in *Cancer Discov* 2016; 6:316-29.

AMG 510 is a small molecule that specifically and irreversibly inhibits $KRAS^{G12C}$ through a unique interaction with the P2 pocket. The inhibitor traps $KRAS^{G12C}$ in the inactive GDP-bound state by a mechanism similar to that described for other $KRAS^{G12C}$ inhibitors. See, for example, Lito P, Solomon M, Li L-S, Hansen R, Rosen N. "Allele-specific inhibitors inactivate mutant KRAS G12C by a trapping mechanism" in Science 2016; 351:604-8. Preclinical studies showed that AMG 510 inhibited nearly all detectable phosphorylation of extracellular signal-regulated kinase (ERK), a key downstream effector of KRAS, leading to durable complete tumor regression in mice bearing KRAS p.G12C tumors. See, for example, Canon J, Rex K, Saiki A Y, et al. "The clinical KRAS(G12C) inhibitor AMG 510 drives anti-tumour immunity" in *Nature* 2019; 575:217-23.

AMG 510 has the following chemical structure:

AMG 510

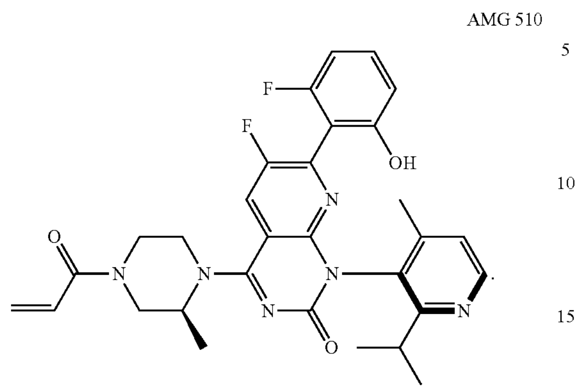

The compound has an atropisomeric chiral center, wherein in the (M)-configuration (shown above) is more active at the target protein than the (P)-configuration.

One synthetic intermediate in the synthesis of AMG 510 is compound A, which has an IUPAC name of 7-chloro-6-fluoro-1-(2-isopropyl-4-methylpyridin-3-yl)pyrido[2,3-d]pyrimidine-2,4(1H,3H)-dione, and a structure of:

compound A

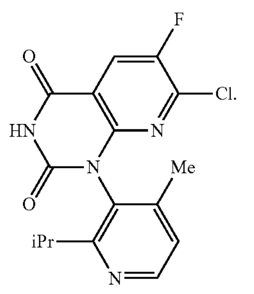

The (P)- and (M)-atropisomers of Compound A have a structure of:

(P)-compound A

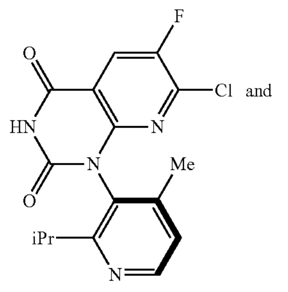

and (M)-compound A

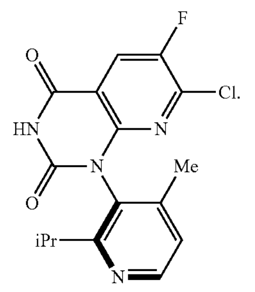

(M)-compound A is carried forward as a feedstock in the synthesis of AMG 510 and (P)-compound A is discarded into a waste stream.

Separation of (M)- and (P)-compound A can be achieved via various means. For example, compound A can be mixed with dibenzoyl tartaric acid (DBTA) to form a DBTA co-crystalt of each of the (P)- and (M)-atropisomers, wherein the crystalline (M)-compound A tartrate is separated from the mixture leaving behind the (P)-compound A tartrate in the mother liquor.

When DBTA salt and (M)-compound crystallization is employed, it produces a waste solution of (P)-compound A and dibenzoyl tartaric acid. This general chiral resolution of compound A using (+)-dibenzoyl-D-tartaric acid [(+)-DBTA; CAS 17026-42-5] is depicted in Scheme 1.

Scheme 1. DBTA resolution of compound A.

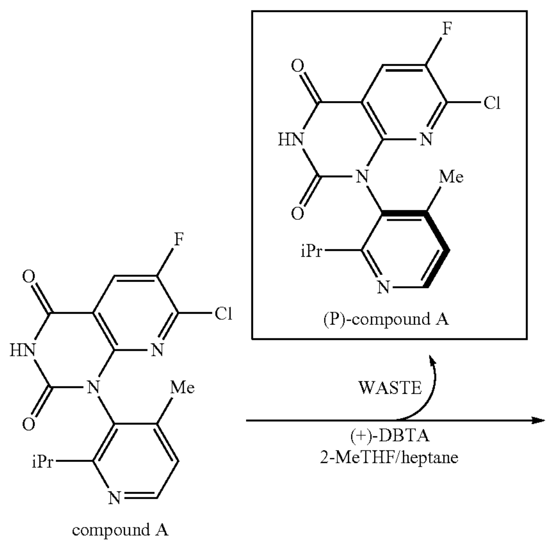

-continued

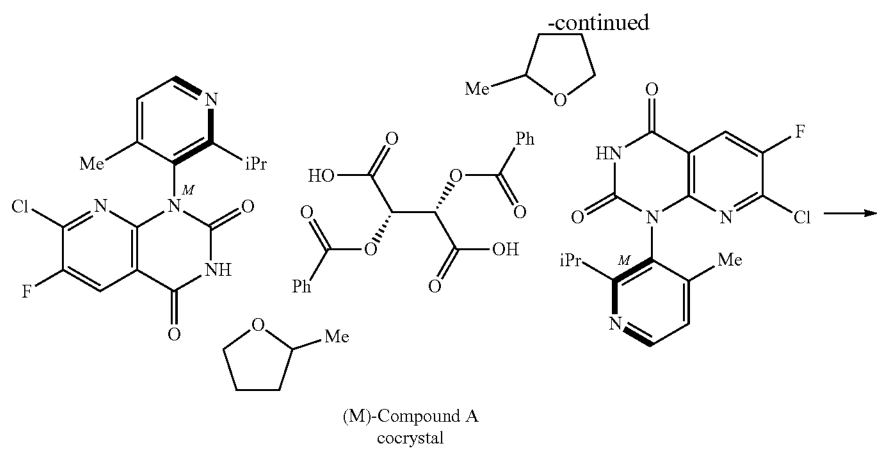

(M)-Compound A cocrystal

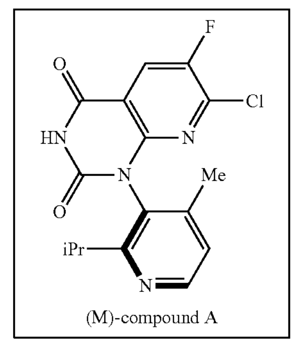

(M)-compound A

Although this process provides (M)-compound A in high stereochemical purity, the maximum theoretical yield is limited to only 50% since half of the material (i.e., (P)-compound A tartrate) remains in the mother liquor, which goes to the waste stream of the process. Moreover, a single (+)-DBTA molecule allows isolation of two (M)-compound A molecules via co-crystal formation, as determined by X-ray crystal analysis. As such, only 0.25 equivalent of DBTA is used to recover 0.5 equivalent of (M)-compound A (racemic compound A: 0.5 equiv. (M)-compound A and 0.5 equiv. (P)-compound A). However, to maximize the enantiomeric excess (% ee) of (M)-compound A and the recovery yield, 3.0 equivalents of (+)-DBTA are charged into the process, leading to 2.75 equivalents wasted into the final liquor stream with (P)-compound A.

In view of the foregoing, there is a need for an efficient, scalable, cost-effective processes to isolate (P)-compound A from a mixture and to recycle (P)-compound A to regenerate the racemic compound A. In addition, there also is a need for recycling and isolating a free acid of a tartrate or a hydrate thereof from a composition comprising a tartrate, (P)-compound A, and an organic solvent.

SUMMARY

The disclosure provides processes comprising heating a composition comprising (P)-compound A or a salt thereof and a solvent to a temperature of 250° C. to 350° C. to form racemized compound A:

(A)

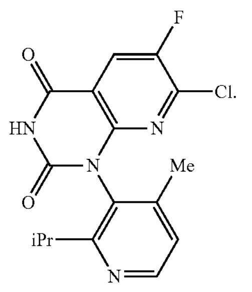

The disclosure also provides processes for isolating (P)-compound A from a composition comprising (P)-compound A, a tartrate, and an organic solvent comprising admixing the composition and an aqueous solution of a base to remove the tartrate and providing a second composition comprising (P)-compound A and the organic solvent.

The disclosure further provides processes for isolating a free acid of a tartrate or a hydrate thereof from a composition comprising a tartrate, (P)-compound A, and an organic solvent:

(P)-compound A

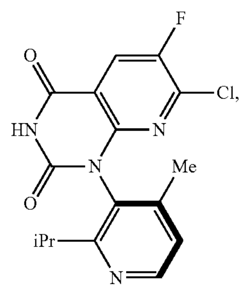

comprising (a) admixing the composition and an aqueous solution of a base to form a dibasic salt of the tartrate in an aqueous phase; (b) separating the aqueous phase from an organic phase comprising the (P)-compound A and the organic solvent; and (c) adding the aqueous phase to an aqueous solution of an acid to form a composition comprising the free acid of the tartrate or a hydrate thereof.

DETAILED DESCRIPTION

Provided herein are processes for obtaining racemized compound A from (P)-compound A or a salt thereof and from mixtures containing (P)-compound A or a salt thereof, a tartrate, and an organic solvent.

(A)

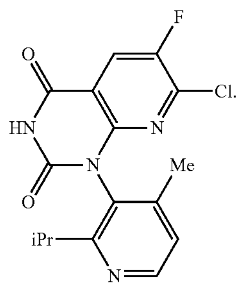

The disclosure provides methods for obtaining (P)-compound A and racemized compound A from feedstocks that had previously been considered to be waste streams.

In some embodiments, the disclosure provides processes for racemizing (P)-compound A or a salt thereof to form a racemized compound A. In some embodiments, the disclosure also provides processes for isolating (P)-compound A from a composition comprising (P)-compound A, a tartrate, and an organic solvent. The racemized compound A and the isolated (P)-compound A obtained from the processes disclosed herein can be used as e.g., starting material, synthetic intermediate, etc., in methods of synthesizing of AMG510.

In some embodiments, the disclosure provides processes for obtaining racemized compound A from (P)-compound A, a cocrystal thereof, or a salt of (P)-compound A or cocrystal thereof. Moreover, in some embodiments, the disclosure provides processes for obtaining racemized compound A from mixtures containing (P)-compound A, a cocrystal thereof, a salt of (P)-compound A or cocrystal thereof, a tartrate, and an organic solvent.

Prior to the present disclosure, the time and energy costs associated with large-scale, efficient recycling/regenerating/racemizing/isolating (P)-compound A were so high, such that the processes were not feasible, particularly on an industrial scale. For example, the energy barrier of rotation around the axial stereocenter to convert the (M)-atropisomer of compound A into the (P)-atropisomer of compound A is calculated to be approximately 42 kcal/mol. This high energy barrier corresponds to a reaction time of longer than $1\times10^9$ years for a typical first order chemical reaction, here a racemization, to proceed to completion when conducted at 20° C.

Moreover, other conventional conditions for isolating (P)-compound A from a mixture containing a tartrate and an organic solvent, such as washing with aqueous solutions of sodium hydroxide or sodium carbonate, or chromatographic separations using silica gel are not suitable for efficient, large-scale operations due to the low yields.

In various embodiments, the disclosed processes provide a source of (M)-compound A that would otherwise end up in waste stream, obtainable by racemizing the waste (P)-compound A to form (M)-compound A. As such, the disclosed process for racemizing (P)-compound A or a salt thereof advantageously improves overall efficiency of processes which use compound A as a feedstock. For example, racemizing (P)-compound A or a salt thereof to generate racemized compound A permits for fewer batches at a reduced cost with less waste.

Process for Racemizing (P)-compound A

The disclosure provides for processes of racemizing (P)-compound A to provide racemized compound A. As used herein, "racemized compound A" refers to compound A which has a lower stereochemical purity (as measured by percent enantiomeric excess- % ee or alternatively as enantiomeric ratio of P/M) than the (P)-compound A starting material. In some cases, the (P)-compound A or salt thereof has an % ee of 50% or more (e.g., 75:25 ratio of PIM), or an % ee of 75% or more (e.g., 87.5:12.5 ratio of PIM), in the composition prior to heating. In some cases, the (P)-compound A or salt thereof has an % ee of 90% or more (e.g., 90%, 91%, 92%, 93%, 94%, 95%, 96%, 97%, 98%, or 99% ee, prior to heating). In various embodiments wherein the (P)-compound is a starting material derived from mother liquors collected from a chiral resolution, the (P)-compound A has a % ee of 70% to 80% (i.e., PIM ratio of 90:10 to 85:15, or 89:11, 88:12, 87:13, or 86:14). In some embodiments, the (P)-compound A or a salt thereof has a 76% ee (i.e., 88:12 PIM).

As described herein, in various embodiments, in conjunction with other above and below embodiments, the composition comprising (P)-compound A and the second composition comprising (P)-compound A further comprises (M)-compound A. In various cases, the composition comprising (P)-compound A or the second composition comprising (P)-compound A comprises an 88:12 P/M mixture (e.g., 24% racemic compound A and 76% (P)-compound A). Moreover, in some embodiments, the disclosed processes further comprise isolating compound A, as a racemate, from the second composition. Without wishing to be bound to any particular theory, it has been discovered that the solubility of racemic compound A is sufficiently different from that of (P)-compound A in various solvents such that racemic compound A solidifies from a solution while (P)-compound A remains in the solution. In some embodiments, the solvent of the solution comprises anisole. In some embodiments, the solid racemic compound A can be separated or isolated from (P)-compound A in the solution by filtration, wherein solid racemic compound A is filtered from solution leaving (P)-compound A in the filtrate. Alternatively, or in addition to, (P)-compound A can be extracted with a suitable organic solvent (e.g., anisole) to provide a solution of (P)-compound A in organic solvent, leaving a solid comprising the racemate compound A.

The resulting racemized compound A provided by the disclosed processes has a stereochemical purity (e.g., % ee) after heating that is lower than that of the starting (P)-compound A. In various embodiments, the racemized compound A has a 50% ee or less after heating. In various embodiments, the racemized compound A has a % ee of 30% or less or after heating. In some embodiments, the racemized compound A has a % ee of 0 to 45%, or 0 to 40%, or 0 to 35%, or 0 to 30%, or 0 to 25%.

The processes disclosed herein to racemize compound A are such that the compound is racemized but with minimal decomposition or degradation as exhibited by the amount of impurities measured in the resulting racemized compound A. Suitable conditions for assessment of impurities of compound A can be found in the examples described below. For example, impurities can be assessed by HPLC, using normal or reverse phase conditions, and chiral or achiral columns. In various embodiments, the racemized compound A comprises less than 10 wt. % of impurities as determined by chromatography, for example, 9 wt. % or less, 8 wt. % or less, 7 wt. % or less, 6 wt. % or less, 5 wt. % or less, 4 wt. % or less, 3 wt. % or less, 2 wt. % or less, 1 wt. % or less, or 0.5 wt. % or less impurities as determined by chromatography. In various embodiments, racemized compound A comprises less than 5 wt. % of impurities as determined by chromatography. In various embodiments, racemized compound A comprises less than 2 wt. % of impurities as determined by chromatography.

The processes for racemizing (P)-compound A comprise heating a composition comprising (P)-compound A or a salt thereof and a solvent to a temperature of 250° C. to 350° C. to form racemized compound A.

Temperature: The processes disclosed herein occur at temperatures not conventionally associated with conditions used during the synthesis of pharmaceutical active ingredients. It has surprisingly been discovered that the disclosed processes can be conducted at the elevated temperatures required to provide a suitable reaction time (e.g., hours or minutes vs. years) such that racemizing (P)-compound A or a salt thereof as described herein is feasible, for example, proceed with suitable yield, particularly on an industrial scale, to realize the cost savings and waste reduction associated with these processes.

In various embodiments, the composition comprising (P)-compound A or a salt thereof and a solvent is heated to a temperature of 250° C. or more, for example, 255° C., 260° C., 265° C., 270° C., 275° C., 280° C., 285° C., 290° C., 295° C., or 300° C. or more. Alternatively, or in addition to, in various embodiments, the disclosed composition is heated to a temperature of 350° C. or less, for example, 345° C., 340° C., 335° C., 330° C., 325° C., 320° C., 315° C., 310° C., or 305° C. or less. Thus, the composition comprising (P)-compound A or a salt thereof and a solvent can be heated to a temperature bound by, and including, any of the aforementioned endpoints (e.g., a temperature of 250 to 350° C., or 255 to 345° C., 260 to 340° C., 265 to 335° C., 270 to 330° C., 275 to 325° C., 280 to 320° C., 285 to 315° C., 290 to 310° C., or 295 to 305° C.).

In some embodiments, the composition comprising (P)-compound A or a salt thereof is heated to a temperature of 300 to 325° C. In some embodiments, the composition comprising (P)-compound A or a salt thereof is heated to a temperature of 305 to 320° C. In some embodiments, the composition comprising (P)-compound A or a salt thereof is heated to a temperature of 310° C. In some embodiments, the composition comprising (P)-compound A or a salt thereof is heated to a temperature of 315° C.

Solvent: The solvent can be any suitable solvent, as described herein. In view of the temperatures of the disclosed process, the solvent(s) desirably is stable at the temperatures of the process. For example, it is well understood that certain solvents can undergo thermal decomposition at high temperatures (e.g., DMSO and (1S,5R)-6,8-dioxabicyclo[3.2.1]octan-4-one (dihydrolevoglucosenone, CYRENE™) can decompose at 300° C.). Solvent decomposition is undesirable since the by-products of the decomposition can lead to by-products and/or lower yields of racemized compound A. Thus, the solvent is selected to have minimal or no thermal decomposition under the conditions of the process.

Moreover, the solvent desirably is inert, for example, the solvent should not interact with (P)-compound A or compound A to result in decomposition of (P)-compound A or compound A or to reduce the chemical or stereochemical yield of the process.

In various embodiments, the organic solvent is a non-polar solvent. As used herein, "non-polar" refers to a solvent having a dielectric constant (s) of 10 or less, when measured at 20 to 25° C. Dielectric constant of most solvents are reported in the literature.

The solvent can have any suitable boiling point provided that the solvent is stable under the conditions of the process (e.g., reaction temperatures and pressures) such that the solvent does not undergo significant thermal decomposition. The solvent can have a boiling point of 80° C. or more, for example, 90° C. or more, 100° C. or more, 110° C. or more, 120° C. or more, 130° C. or more, 140° C. or more, 150° C. or more, 160° C. or more, 170° C. or more, 180° C. or more, 190° C. or more, or 200° C. or more. Alternatively, or in addition to, the solvent can have a boiling point of 320° C. or less, for example, 310° C. or less, 300° C. or less, 290° C. or less, 280° C. or less, 270° C. or less, 260° C. or less, 250° C. or less, 240° C. or less, 230° C. or less, 220° C. or less, or 210° C. or less. As such, the solvent can have a boiling point bounded by, and including, any of the aforementioned endpoints (e.g., 80 to 320° C., 90 to 310° C., 100 to 300° C., 110 to 290° C., 120 to 280° C., 130 to 270° C., 140 to 260° C., 150 to 250° C., 160 to 240° C., 170 to 230° C., 180 to 220° C., or 190 to 210° C.).

In some cases, the solvent comprises one or more organic solvents. In instances when the solvent comprises more than one solvent, the properties of the bulk solvent are as described herein for an individual solvent (e.g., stable, inert, minimal decomposition, and the like).

Contemplated nonpolar solvents include, but are not limited to, anisole, benzene, bromobenzene, carbon tetrachloride, chlorobenzene, chloroform, cyclohexane, dibutyl ether, dichlorobenzene, dibenzyl ether, dichloromethane, dioxane, diphenyl ether, 1-octadecene, tetrahydrofuran, 2-methyl tetrahydrofuran, toluene, trichloroethylene, and xylene, or a combination thereof. In various embodiments, the solvent comprises diphenyl ether, 1-octadecene, anisole, or a combination thereof. In some embodiments the solvent comprises diphenyl ether. In some embodiments, the solvent comprises 1-octadecene. In some embodiments, the solvent comprises anisole.

Pressure: In various embodiments, the racemization via heating is conducted at an elevated pressure (greater than 0.1 MPa). In some embodiments, the heating is conducted at 1.5 MPa or more, for example, 1.6 MPa or more, 1.7 MPa or more, 1.8 MPa or more, 1.9 MPa or more, 2.0 MPa or more, 2.1 MPa or more, 2.2 MPa or more, 2.3 MPa or more, 2.4 MPa or more, 2.5 MPa or more, 2.6 MPa or more, 2.7 MPa or more, 2.8 MPa or more, 2.9 MPa or more, 3.0 MPa or more, 3.1 MPa or more. 3.2 MPa or more, 3.3 MPa or more, 3.4 MPa or more, or 3.5 MPa or more. Alternatively, or in addition to, in some embodiments, the heating is conducted at 7.0 MPa or less, for example, 6.9 MPa or less, 6.8 MPa or less, 6.7 MPa or less, 6.6 MPa or less, 6.5 MPa or less, 6.4 MPa or less, 6.3 MPa or less, 6.2 MPa or less, 6.1 MPa or less, 6.0 MPa or less, 5.9 MPa or less, 5.8 MPa or less, 5.7 MPa or less, 5.6 MPa or less, 5.5 MPa or less, 5.4 MPa or less, 5.3 MPa or less, 5.2 MPa or less, 5.1 MPa or less, 5.0 MPa or less, 4.9 MPa or less, 4.8 MPa or less, 4.7 MPa or less, 4.6 MPa or less, 4.5 MPa or less, 4.4 MPa or less, 4.3 MPa or less, 4.2 MPa or less, 4.1 MPa or less, 4.0 MPa or less, 3.9 MPa or less, 3.8 MPa or less, 3.7 MPa or less, or 3.6 MPa or less. Thus, the heating can be conducted at any pressure bound by and including any of the aforementioned endpoints. For example, the heating can be conducted at a pressure of 1.5 to 7.0 MPa, 1.6 to 6.9 MPa, 1.7 to 6.8 MPa, 1.8 to 6.7 MPa, 1.9 to 6.6 MPa, 2.0 to 6.5 MPa, 2.1 to 6.4 MPa, 2.2 to 6.3 MPa, 2.3 to 6.2 MPa, 2.4 to 6.1 MPa, 2.5 to 6.0 MPa, 2.6 to 5.9 MPa, 2.7 to MPa, 2.8 to 5.7 MPa, 2.9 to 5.6 MPa, 3.0 to 5.5 MPa, 3.1 to 5.4 MPa, 3.2 to 5.3 MPa, 3.3 to 5.2 MPa, 3.4 to MPa, 3.5 to 5.0 MPa, 3.6 to 4.9 MPa, 3.7 to 4.8 MPa, 3.8 to 4. MPa 7, 3.9 to 4.6 MPa, 4.0 to 4.5 MPa, 4.1 to 4.4 MPa, or 4.2 to 4.3 MPa.

Reaction Time: The disclosed processes provide a commercially relevant reaction time for racemizing compound A. The processes disclosed herein provide racemized compound A on a reaction time scale of hours or minutes, rather than years. In various embodiments, the heating occurs for 5 minutes to 12 hours, for example, 15, 30, or 45 minutes or more. In some cases, the heating occurs for 12 hours or less, for example, 11.5 hours or less, 11 hours or less, 10.5 hours or less, 10 hours or less, 9.5 hours or less, 9 hours or less, 8.5 hours or less, 8 hours or less, 7.5 hours or less, 7 hours or less, 6.5 hours or less, 6 hours or less, 5.5 hours or less, 5 hours or less, 4.5 hours or less, 4 hours or less, 3.5 hours or less, 3 hours or less, 2.5 hours or less, 2 hours or less, 1.5 hours or less, or 1 hour or less. In various embodiments, the heating occurs for 1 to 4 hours.

Use of Racemized Compound A: As described herein, the disclosed processes of racemizing (P)-compound A can be incorporated into the synthesis of AMG 510 to obtain (M)-compound (A), which can be taken on in the synthesis of AMG 510, e.g., as disclosed in U.S. Pat. No. 10,519,146 (Example 41-1).

In various embodiments, the disclosed processes further comprise subjecting the racemized compound (A) to a chiral resolution using a tartrate (such as dibenzoyl tartaric acid) to crystallize (M)-compound A as a tartrate crystal, thereby separating (P)-compound A and (M)-compound A. (M)-Compound A can then be used in the synthesis of AMG 510 (e.g., converted to AMG 510). The mother liquor from the crystallization step comprising (P)-compound A can be taken on to recycle again via a racemization process as disclosed herein.

Isolation of (M)-compound A from racemized compound A can be accomplished via a number of methods other than chiral crystallization with a tartrate. In various embodiments, racemized compound A can be subjected to simulated moving bed (SMB) chromatography to separate (P)-compound A and (M)-compound A.

Other tartrates that can be used in the disclosed processes include, for example, (+)-di-O,O'-toluoyl-(D)-tartaric acid, (−)-di-O,O'-toluoyl-(L)-tartaric acid, (+)-di-O,O'-benzoyl-(D)-tartaric acid, and (−)-di-O,O'-benzoyl-(L)-tartaric acid.

Process for Isolating (P)-compound A from a Tartrate Solution

Other conventional methods for isolating (P)-compound A from a composition containing significant concentrations of a tartrate were not feasible. For example, the efficient removal of high levels of dibenzoyl tartaric acid, DBTA (about 23 wt. %), on a large scale, presented a significant challenge rendering conventional methods impracticable. Removal of DBTA was challenging as there was significant precipitation of the DBTA and poor partitioning of (P)-compound A between the organic and aqueous layers, leading to low yields of isolated (P)-compound A.

It has been found that isolation of (P)-compound A from a composition comprising tartrate, (P)-compound A, and an organic solvent can be performed on a commercial synthesis scale using the appropriate base and extraction techniques. Thus, provided herein are processes of isolating (P)-compound A from a composition comprising (P)-compound A, a tartrate, and an organic solvent, the process comprising admixing the composition and an aqueous solution of a base to remove the tartrate (into the aqueous solution of the base) and providing a second composition containing (P)-compound A and the organic solvent. In various embodiments, the composition comprising (P)-compound A, tartrate, and organic solvent is added to the aqueous base solution. In various embodiments, the tartrate is dibenzoyl tartaric acid (e.g., (+)-DBTA). In various embodiments, the composition comprising (P)-compound A, a tartrate, and an organic solvent comprises 10-50 wt. % tartrate, for example, 15-30 wt. % tartrate, or 20-25 wt. % tartrate. In some embodiments, the composition comprises 23 wt % tartrate.

Base: The disclosed processes comprise admixing aqueous solution of a base with the composition comprising (P)-compound A, a tartrate, and an organic solvent. This admixing results in a two phase system, where the aqueous base solution deprotonates the tartrate in the composition and solubilizes it in the aqueous phase, leaving the (P)-compound A in the organic phase, with the organic solvent. The phases can be separated, and the organic phase of (P)-compound A can be used in further processes as disclosed herein, e.g., in the racemization processed discussed above.

Suitable bases are bases that can deprotonate the tartrate to form a tartrate salt that is soluble in an aqueous solution. For example, the aqueous base solution is capable of solubilizing the deprotonated tartrate. If the base does not have suitable solubility in the aqueous solution or provide suitable solubility of the ionic species that are present (or formed), then the tartrate forms precipitates in the aqueous solution which lower the efficiency the process thereby resulting in lower yields of isolated (P)-compound A.

Contemplated bases include, for example, a hydroxide, a phosphate, a carbonate or a hydrogen carbonate salt of an alkali or alkaline earth metal, and a combination thereof. In some embodiments, the base is selected from the group consisting of sodium hydroxide, sodium carbonate, potassium carbonate, dipotassium phosphate, and a combination thereof. In various embodiments, the base is a potassium salt. In some embodiments, the base is a an alkali carbonate salt. In some embodiments, the base is potassium carbonate (K 2 CO 3). Without wishing to be bound to any particular theory, potassium carbonate (K 2 CO 3) provides suitable solubility of the tartrate salt, and also provides an effective phase separation between the organic phase and aqueous phase under the process conditions thereby advantageously providing minimal precipitation and suitable yields of (P)-compound A isolation, in some cases greater than 90% recovery from the composition.

In various cases, the concentration of the aqueous base solution is 10 wt. % or more, for example, 11 wt. % or more, 12 wt. % or more, 13 wt. % or more, 14 wt. % or more, 15 wt. % or more, 16 wt. % or more, 17 wt. % or more, 18 wt. % or more, 19 wt. % or more, 20 wt. % or more, 21 wt. % or more, 22 wt. % or more, 23 wt. % or more, 24 wt. % or more, or 25 wt. % or more. In various cases, the concentration of the aqueous base solution typically is 35 wt. % or less, for example, 34 wt. % or less, 33 wt. % or less, 32 wt. % or less, 31 wt. % or less, 30 wt. % or less, 29 wt. % or less, 28 wt. % or less, 27 wt. % or less, or 26 wt. % or less. The aqueous base solution can have a concentration bounded by, and including any of the aforementioned endpoints (e.g., 10 to 35 wt. %, 11 to 34 wt. %, 12 to 33 wt. %, 13 to 32 wt. %, 14 to 31 wt. %, 15 to 30 wt. %, 16 to 29 wt. %, 17 to 28 wt. %, 18 to 27 wt. %, 19 to 26 wt. %, 20 to 25 wt. %, 21 to 24 wt. %, or 22 to 23 wt. %). In some specific cases when the base is potassium carbonate, the aqueous solution of base can have a concentration of 10 to 20 wt. % potassium carbonate in water. For example, in various cases, the base concentration can be 10 wt. %, 11 wt. %, 12 wt. %, 13 wt. %, 14 wt. %, 15 wt. %, 16 wt. %, 17 wt. %, 18 wt. %, 19 wt. %, or 20 wt. % potassium carbonate in water.

In various embodiments, the base is present in an amount of 2 or more molar equivalents per mole (P)-compound A (e.g., 2.5 or more, 3 or more, 3.5 or more, 4 or more, or 4.5 or more molar equivalents per mole (P)-compound A).

In some embodiments, the composition comprising the (P)-compound A, tartrate, and organic solvent and the aqueous solution of the base are present at a volume ratio of at least 0.5:1. In some embodiments, the composition comprising the (P)-compound A, tartrate, and organic solvent and the aqueous solution of the base are present ata volume ratio of 1:1 to 2:1. In some cases, the volume ratio is 2:1 composition to aqueous solution. In some cases where the volume ratio is 1:1 or greater, the amount of base wt. % is at least 10 wt. % in the aqueous solution. In various embodiments, the aqueous base solution is 20 wt. % potassium carbonate and the composition comprising the (P)-compound A, tartrate, and organic solvent and the aqueous solution of the base are present at a volume ratio of 2:1.

In various embodiments, the disclosed processes for isolating (P)-compound A further comprises a washing step of the organic phase (the second composition) with water to remove residual aqueous soluble species (e.g., tartrate salts). In some embodiments, the water and the second composition are present at a volumetric ratio of 0.5:1 for the washing step.

In various embodiments, the resulting composition of (P)-compound A and organic solvent can further be subjected to distilling to reduce the volume of the composition containing the (P)-compound A. In various embodiments, the distillation step results in a reduced volume of 30% to 50% of the volume of the starting composition. For example, reduced volume composition can have a volume of 30% or more of the volume of the washed composition (e.g., 30%, 31%, 32%, 33%, 34%, 35%, 36%, 37%, 38%, 39%, 40%, 41%, 42%, 43%, 44%, 45%, 46%, 47%, 48%, 49% or 50% k of the volume of the washed composition). In various embodiments, the composition being distilled has been washed first as described above. In some embodiments, the composition being distilled has not been washed first.

The reduced volume composition can then be subjected to additional processing, as needed, for example, crystallization and/or racemization. In some instances, the (P)-compound A is crystallized from the reduced volume composition to form crystalline (P)-compound A. In some instances, wherein the (P)-compound A is crystallized, an antisolvent can be added to facilitate crystallization of the (P)-compound A. For example, an antisolvent (e.g., heptane) may be added to the reduced volume from either the reduced volume second composition and/or the reduced volume washed composition. In some instances, the reduced volume composition is subjected to any one of the disclosed racemization processes disclosed herein.

Process for Isolating Tartrate Free Acid or a Hydrate Thereof

The present disclosure provides a process for isolating a free acid of a tartrate or a hydrate thereof from a composition comprising a tartrate, (P)-compound A, and an organic solvent comprising (a) admixing the composition and an aqueous solution of a base to form a dibasic salt of the tartrate in an aqueous phase; (b) separating the aqueous phase from an organic phase comprising the (P)-compound A and the organic solvent; and (c) adding the aqueous phase to an aqueous solution of an acid to form a composition comprising the free acid of the tartrate or a hydrate thereof.

In some embodiments, in conjunction with other above or below embodiments, the process further comprises washing the aqueous phase with a second organic solvent to form a washed aqueous phase prior to performing step (c). In these embodiments wherein a second organic solvent is present, the second organic solvent can be any suitable organic solvent. Desirably, the second organic solvent is immiscible with water to an extent such that a biphasic system is formed. For example, contemplated solvents suitable for the second organic solvent include ethyl acetate, isopropyl acetate, methyl ethyl ketone, dichloromethane, methyl tert-butyl ether, toluene, tetrahydrofuran, 2-methyltetrahydrofuran, and a combination thereof. In various embodiments, the second organic solvent is selected from the group consisting of toluene, 2-methyltetrahydrofuran, and a combination thereof. In some embodiments, the second organic solvent is toluene.

In various embodiments, the composition comprising the tartrate, (P)-compound A, and organic solvent(s) is a composition from a synthesis of AMG 510, as described herein. As such, in these embodiments, the properties and characteristics of the composition (e.g., tartrate concentration, base, concentration of base) are the same as those described herein for processes for isolating (P)-compound A. Heretofore, this composition was considered to be waste stream from the synthesis of AMG 510.

The disclosure provides processes for recycling tartrates. In some embodiments the tartrate comprises DBTA, for example, (+)-DBTA (also referred to as D-DBTA), as described herein having the formula:

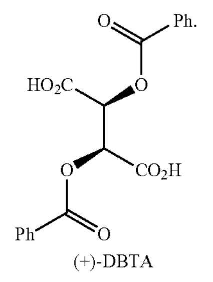 [SMILES: O=C(O[C@H](C(=O)O)[C@H](OC(=O)c1ccccc1)C(=O)O)c1ccccc1]

(+)-DBTA

For example, in some embodiments, the organic residual liquor from the synthesis of AMG 510 comprising (+)-DBTA and (P)-compound A is extracted into an aqueous phase, by adding a suitable amount of base (e.g., 15 wt. % $K_2$ $CO_3$ aq.) and optionally washed with a second organic solvent. The aqueous basic phase is then separated, wherein the tartrate salt is then crystallized by addition to an excess of an acid solution in water. An illustrative embodiment is summarized in Scheme 2.

Scheme 2. Isolation of (+)-DBTA monohydrate

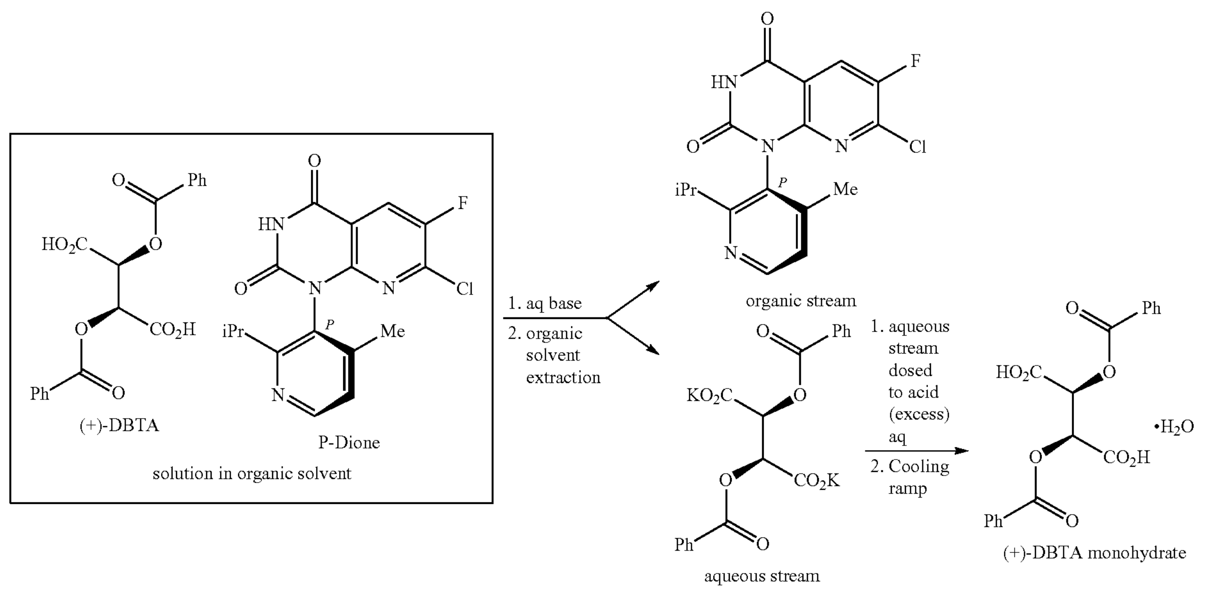

In some embodiments, the process further comprises isolating the free acid of the tartrate or hydrate thereof from the composition. For example, in some embodiments, the process comprises crystallizing the free acid of the tartrate or hydrate thereof and filtering the resulting free acid of the tartrate or hydrate thereof. In some embodiments, in conjunction with other above or below embodiments, the tartrate free acid is isolated as a hydrate.

As used herein, the term hydrate refers to the chemical entity formed by the integration of water and a compound, including, for example, hemi-hydrates, monohydrate, dihydrates, trihydrates, etc.

In some embodiments, the isolated tartrate free acid is (+)-DBTA monohydrate. In some embodiments, in conjunction with other above or below embodiments, the disclosed processes provide (+)-DBTA monohydrate crystals of cylindrical shape having a length of about 70 μm and a width of about 20 μm (e.g., 67×17 μm).

The disclosed process provides the isolated tartrate free acid, or hydrate thereof, in high chemical purity, as well as stereochemical purity. By way of example, in some embodiments, the processes herein provide (+)-DBTA monohydrate having a chemical purity of 95% or higher (e.g., 95%, 96%, 97%, 98%, 99%, 99.5% or higher) with a high % ee, for example, 90% ee or greater (90, 91, 92, 93, 94, 95, 96, 97, 98, 99, 99.5 99.9, or 100% ee).

The isolated tartrate is suitable for use in other processes (e.g., preparing AMG 510). For example, in some embodiments, the disclosed processes herein further comprise admixing the isolated (+)-DBTA monohydrate with racemic compound A to form a co-crystal of (+)-DBTA and (M)-compound A; separating the co-crystal of (+)-DBTA and (M)-compound A from (P)-compound A; and using the co-crystal of (+)-DBTA and (M)-compound A to synthesize AMG 510.

Base: The disclosed processes comprise admixing an aqueous solution of base with a composition comprising a tartrate, (P)-compound A, and an organic solvent to form a dibasic salt of the tartrate. The base can be any suitable base such that a dibasic salt of the tartrate is formed. In some embodiments, the base comprises an alkali carbonate salt, for example, potassium carbonate ($K_2CO_3$). In other embodiments, in conjunction with other above or below embodiments, the base is selected from the group consisting of a hydroxide, a phosphate, a carbonate, or a hydrogen carbonate salt of an alkali or alkaline earth metal (e.g., sodium hydroxide, potassium hydroxide, sodium carbonate, potassium carbonate, dipotassium phosphate, and a combination thereof). In some embodiments, the base is potassium carbonate and is present as a 15 wt. % aqueous solution. As described herein, in various embodiments herein, the dibasic tartrate is dipotassium salt of (+)-DBTA.

The base is present in any suitable amount such that the dibasic salt of the tartrate is formed. Typically, 2 to 5 molar equivalents of base are present per mole of tartrate. In some embodiments, in conjunction with other above or below embodiments, the aqueous solution of base is present at a volume ratio of 2:1.

Acid: The processes disclosed herein comprise adding the basic aqueous phase comprising a dibasic salt of a tartrate in an aqueous phase to a solution of an acid to form a composition comprising a free acid of the tartrate or a hydrate thereof. The acid can be any suitable acid such that the free acid of the tartrate is formed. It is desirable that the acid has a pKa below 1.8. Suitable acids include, for example, hydrochloric acid and sulfonic acids having a pKa below 1.8. In some embodiments, the acid is selected in from the group consisting of hydrochloric acid, hydrobromic acid, hydroiodic acid, nitric acid, phosphoric acid, picric acid, sulfuric acid, methanesulfonic acid, methanesulfonic acid, benzenesulfonic acid, para-toluenesulfonic acid, trifluoromethanesulfonic acid, trifluoroacetic acid, and a combination thereof. In some embodiments, the acid comprises hydrochloric acid.

Desirably, the basic aqueous phase is added to the aqueous solution of acid to form the tartrate free acid. Without wishing to be bound to any particular theory, it has been discovered that this order of addition optimizes the formation of the free acid of the tartrate, and minimizes the formation of the undesirable mono-alkaline salt of the tartrate. For example, in the synthesis of AMG 510 the use of an alkaline salt of (+)-DBTA (e.g., mono-potassium (+)-DBTA) presents an increased process risk on production, particularly during large scale processes, since the monoalkaline salts have lower solubility in organic solvent compared to their free form, precipitate from solution resulting in process failures possibly leading to the waste entire batches of API.

In the case of adding a (+)-DBTA di-potassium salt basic aqueous stream to an aqueous solution of excess strong acid, it is believed that during DBTA crystallization the pH should be maintained to be lower than the pKa of fully-protonated DBTA (pKa 1.85, 2×$CO_2H$) in order to prohibit the formation of a mono-alkaline salt. By way of contrast, if the order of addition is reversed such that the acid solution is added to the basic stream, the internal pH leading during DBTA crystallization will start from a pH of 9 and plateau at a pH of about 4.9 as the first carboxylic acid moiety is protonated. The resulting mono-alkaline DBTA salt precipitates from solution forming a slurry, at which point charging the reaction with extra acid (HCl) to drop the pH below 1 does not impact the stable mono-alkaline salt of (+)-DBTA that has precipitated from solution.

In view of the foregoing, the acid is present in a suitable amount to ensure that the free acid of the tartrate free acid is formed. In some embodiments, the acid is present in an amount of at least 30±5 mol equivalents based upon the mol of tartrate present. For example, in some embodiments the acid is present in an amount of 25, 26, 27, 28, 29, 30, 31, 32, 33, 34, or 35 mol equivalents based upon the mol of tartrate present. In some embodiments, the pH of the aqueous solution of an acid is maintained at all times at a pH of less than 2, 1.9, 1.85, 1.7, 1.5, 1.3, or 1. In some embodiments, the pH of the aqueous solution of an acid is maintained at a pH of less than 1.85. In some embodiments, the pH of the aqueous solution of an acid is maintained at a range bounded by, and including any of the aforementioned values (e.g., 2 to 1, 1.85 to 1, 2 to 1.5, etc.).

Temperature: For the processes disclosed herein, wherein the aqueous phase is added to the aqueous solution of an acid at a temperature of 35 to 55° C. In some embodiments, in conjunction with other above or below embodiments, the temperature is 35 to 55° C. (e.g., 35, 36, 37, 38, 39, 40, 41, 42, 43, 44, 45, 46, 47, 48, 49, 50, 51, 52, 53, 54, or 55° C.). In some embodiments, in conjunction with other above or below embodiments, the temperature is 40 to 50° C. In some embodiments, the temperature is 45° C.

In some embodiments, in conjunction with other above or below embodiments, the composition comprising the free acid of the tartrate or a hydrate thereof is cooled to a temperature of 5 to 20° C. (e.g., 5, 6, 7, 8, 9, 10, 11, 12, 13, 14, 15, 16, 17, 18, 19, or 20° C.). In some embodiments, composition comprising the free acid of the tartrate or a hydrate thereof is cooled to a temperature of 10° C. In various embodiments, the composition comprising the free acid of the tartrate or a hydrate thereof is cooled over a period of 1 hour or longer (e.g., 1 to 12 hours), for example, 2, 3, 4, 5, 6, 7, 8, 9, 10, 11, or 12 hours. In some embodiments, the composition comprising the free acid of the tartrate or a hydrate thereof is cooled over a period of 5 hours.

EMBODIMENTS

1. A process comprising:
heating a composition comprising (P)-compound A or a salt thereof and a solvent to a temperature of 250° C. to 350° C. to form racemized compound A:

(A)

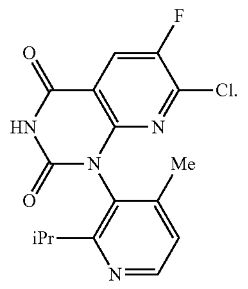

2. The process of embodiment 1, wherein the solvent comprises a nonpolar solvent.
3. The process of embodiment 1 or 2, wherein the solvent is selected from the group consisting of diphenyl ether, 1-octadecene, anisole, and a combination thereof.
4. The process of any one of embodiments 1-3, wherein the solvent comprises anisole.
5. The process of any one of embodiments 1-4, wherein the composition is heated to a temperature of 300° C. to 325° C.
6. The process of embodiment 5, wherein the temperature is 305° C. to 320° C.
7. The process of embodiment 5, wherein the temperature is 310° C.
8. The process of embodiment 5, wherein the temperature is 315° C.
9. The process of any one of embodiments 1-8, wherein the heating is performed at a pressure of 1.7 to 7.0 MPa.
10. The process of any one of embodiments 1-9, wherein (P)-compound A has a % ee of 50% or more in the composition prior to heating.
11. The process of embodiment 10, wherein (P)-compound A has a % ee of 75% or more in the composition prior to heating.
12. The process of embodiment 10, wherein (P)-compound A has a % ee of 90% or more in the composition prior to heating.
13. The process of any one of embodiments 1-11, wherein racemized compound A has a % ee of 50% or less.
14. The process of embodiment 13, wherein racemized compound A has a % ee of 30% or less.
15. The process of any one of embodiments 1-14, wherein racemized compound A, after heating, comprises less than 10 wt % of impurities as determined by chromatography.
16. The process of embodiment 15, wherein racemized compound A, after heating, comprises less than 5 wt % of impurities as determined by chromatography.
17. The process of embodiment 16, wherein racemized compound A, after heating, comprises less than 2 wt % of impurities as determined by chromatography.
18. The process of any one of embodiments 1-17, wherein the heating occurs for 5 minutes to 12 hours.
19. The process of embodiment 18, wherein the heating occurs for 1 hour to 4 hours.

20. The process of any one of embodiments 1-19, further comprising subjecting the racemized compound A to simulated moving bed chromatography to separate (P)-compound A and (M)-compound A.

21. The process of any one of embodiments 1-19, further comprising subjecting the racemized compound A to a chiral resolution using a tartrate to separate (P)-compound A and (M)-compound A.

22. The process of embodiment 20 or 21, further comprising converting the (M)-compound A to AMG 510.

23. A process for isolating (P)-compound A from a composition comprising (P)-compound A, a tartrate, and an organic solvent:

(A)

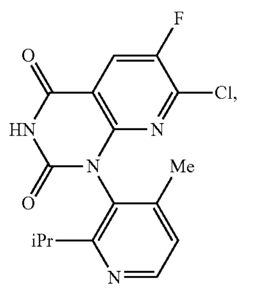

comprising:

admixing the composition and an aqueous solution of a base to remove the tartrate and providing a second composition comprising (P)-compound A and the organic solvent.

24. The process of embodiment 23, wherein the tartrate comprises dibenzoyl tartaric acid ("DBTA").

25. The process of embodiment 24, wherein the tartrate is (+)-DBTA

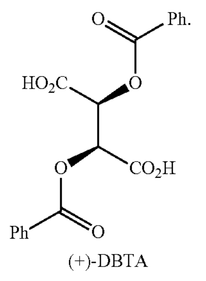 [SMILES: O=C(O[C@H](C(=O)O)[C@H](OC(=O)c1ccccc1)C(=O)O)c1ccccc1]

26. The process of any one of embodiments 23-25, wherein the composition comprises 10-50 wt % tartrate.

27. The process of embodiment 26, wherein the composition comprises 15-30 wt % tartrate.

28. The process of embodiment 26, wherein the composition comprises 20-25 wt % tartrate.

29. The process of any one of embodiments 23-28, wherein the base is selected from the group consisting of a hydroxide, a phosphate, a carbonate or a hydrogen carbonate salt of an alkali or alkaline earth metal, and a combination thereof.

30. The process of embodiment 29, wherein the base is selected from the group consisting of sodium hydroxide, sodium carbonate, potassium carbonate, dipotassium phosphate, and a combination thereof.

31. The process of any one of embodiments 23-30, wherein the base comprises an alkali carbonate salt.

32. The process of embodiment 31, wherein the alkali carbonate salt is potassium carbonate ($K_2CO_3$).

33. The process of any one of embodiments 23-32, wherein the base is present in an amount of 2 to 5 molar equivalents per mole (P)-compound A.

34. The process of any one embodiments 23-32, wherein the composition and the aqueous solution of the base are present at a volume ratio of 2:1.

35. The process of embodiment 23-34, further comprising distilling the second composition to form a reduced volume second composition.

36. The process of embodiment 35, further comprising crystallizing (P)-compound A from the reduced volume second composition to form crystalline (P)-compound A.

37. The process of embodiment 36, wherein the crystallizing comprises using an antisolvent.

38. The process of embodiment 37, wherein the antisolvent comprises heptane.

39. The process of any one of embodiments 35-38, further comprising subjecting the reduced volume second composition or the crystalline (P)-compound A to the process of any one of embodiments 1-21 to form racemized compound A.

40. The process of any one of embodiments 23-39, further comprising washing the second composition with water to form a washed composition comprising (P)-compound A and the organic solvent.

41. The process of embodiment 40, wherein the water and the second composition are present at a volume ratio of 0.5:1.

42. The process of embodiment 40 or 41, further comprising distilling the washed composition to form a reduced volume washed composition comprising (P)-compound A having a volume of 30% to 50% of the volume of the washed composition.

43. The process of embodiment 42, further comprising crystallizing (P)-compound A from the reduced volume washed composition to form crystalline (P)-compound A.

44. The process of embodiment 43, wherein the crystallizing comprises using an antisolvent.

45. The process of embodiment 44, wherein the antisolvent comprises heptane.

46. The process of any one of embodiments 36-38 and 40-44, further comprising subjecting the reduced volume washed composition comprising (P)-compound A or the crystalline (P)-compound A to the process of any one of embodiments 1-21 to form racemized compound A.

47. The process of any one of embodiments 23-46, wherein the composition comprising (P)-compound A further comprises (M)-compound A, and the second composition comprising (P)-compound A further comprises (M)-compound A.

48. The process of embodiment 47, wherein the composition, the second composition, or both comprises (P)-compound A and (M)-compound A in a 88:12 PIM ratio.

49. The process of embodiment 47 or 48, further comprising isolating compound A, as a racemate, from the second composition by forming solid racemic compound A in the second composition and filtering the resulting mixture to isolate the racemate leaving (P)-compound A in the filtrate.

50. The process of embodiment 49, wherein forming solid racemic compound A comprises adding anisole to the second composition to precipitate racemic compound A.

51. A process for isolating a free acid of a tartrate or a hydrate thereof from a composition comprising a tartrate, (P)-compound A, and an organic solvent:

(P)-compound A

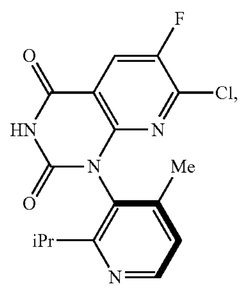

comprising:

(a) admixing the composition and an aqueous solution of a base to form a dibasic salt of the tartrate in an aqueous phase;

(b) separating the aqueous phase from an organic phase comprising the (P)-compound A and the organic solvent; and (c) adding the aqueous phase to an aqueous solution of an acid to form a composition comprising the free acid of the tartrate or a hydrate thereof.

52. The process of embodiment 51, wherein the tartrate comprises dibenzoyl tartaric acid ("DBTA").

53. The process of embodiment 52, wherein the tartrate is (+)-DBTA

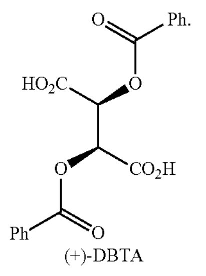 [SMILES: O=C(O[C@H](C(=O)O)[C@H](OC(=O)c1ccccc1)C(=O)O)c1ccccc1]

(+)-DBTA

54. The process of any one of embodiments 51-53, wherein the composition comprises 10-50 wt % tartrate.

55. The process of embodiment 54, wherein the composition comprises 15-30 wt % tartrate.

56. The process of embodiment 54, wherein the composition comprises 20-25 wt % tartrate.

57. The process of any one of embodiments 51-56, wherein the base is selected from the group consisting of a hydroxide, a phosphate, a carbonate or a hydrogen carbonate salt of an alkali or alkaline earth metal, and a combination thereof.

58. The process of embodiment 57, wherein the base is selected from sodium hydroxide, sodium carbonate, potassium carbonate, dipotassium phosphate, and a combination thereof.

59. The process of any one of embodiments 51-58, wherein the base comprises an alkali carbonate salt.

60. The process of embodiment 58 or 59, wherein the alkali carbonate salt is potassium carbonate ($K_2CO_3$).

61. The process of any one of embodiments 51-60, wherein the base is present in an amount of 2 to 5 molar equivalents per mole tartrate.

62. The process of any one embodiments 51-61, wherein the composition and the aqueous solution of the base are present at a volume ratio of 2:1.

63. The process of any one of embodiments 60-62, wherein the potassium carbonate is present as a 15 wt. % aqueous solution.

64. The process of any one of embodiments 51-63, further comprising washing the aqueous phase with a second organic solvent to form a washed aqueous phase prior to performing step (c).

65. The process of embodiment 64, wherein the second organic solvent is selected from the group consisting of toluene, 2-methyltetrahydrofuran, and a combination thereof.

66. The process of embodiment 65, wherein the second organic solvent is toluene.

67. The process of any one of embodiments 51-66, wherein the acid is present in an amount of at least 25 mol equivalents, based upon mol tartrate.

68. The process of any one of embodiments 51-67, wherein the acid is selected from the group consisting of hydrochloric acid, hydrobromic acid, hydroiodic acid, nitric acid, phosphoric acid, picric acid, sulfuric acid, methanesulfonic acid, benzenesulfonic acid, para-toluenesulfonic acid, trifluoromethanesulfonic acid, trifluoroacetic acid, and a combination thereof.

69. The process of embodiment 68, wherein the acid comprises hydrochloric acid.

70. The process of any one of embodiments 51-69, wherein the aqueous phase is added to the aqueous solution of acid at a temperature of 35 to 55° C.

71. The process of embodiment 70, wherein the temperature is 40 to 50° C.

72. The process of embodiment 70, wherein the temperature is 45° C.

73. The process of any one of embodiments 51-72, further comprising cooling the composition formed in step (c).

74. The process of embodiment 73, wherein the composition formed in step (c) is cooled to a temperature of 5 to 20° C.

75. The process of embodiment 74, wherein the composition formed in step (c) is cooled to a temperature of 10° C.

76. The process of embodiment 74 or 75, wherein the composition formed in step (c) is cooled over a period of 1 hour or longer.

77. The process of any one of embodiments 51-76, further comprising isolating the free acid of the tartrate or hydrate thereof from the composition of step (c).

78. The process of embodiment 77, wherein the isolating comprises crystallizing the free acid of the tartrate or hydrate thereof and filtering the resulting crystalline free acid of the tartrate or hydrate thereof.

79. The process of any one of embodiments 51-78, wherein the free acid of the tartrate is a hydrate.

80. The process of any one of embodiments 51-79, wherein the free acid of the tartrate is (+)-DBTA monohydrate.

81 The process of embodiment 80, wherein the isolated (+)-DBTA monohydrate has a purity of 95% or higher.

82. The process of embodiment 81, wherein the isolated (+)-DBTA monohydrate comprises less than 0.5 wt. % of the mono potassium salt of (+)-DBTA.
83. The process of any one embodiments 80-82, further comprising admixing the isolated (+)-DBTA monohydrate with racemic compound A to form a co-crystal of (+)-DBTA and (M)-compound A; separating the co-crystal of (+)-DBTA and (M)-compound A from (P)-compound A; and using the co-crystal of (+)-DBTA and (M)-compound A to synthesize AMG 510.

EXAMPLES

The following examples further illustrate the disclosed processes, but of course, should not be construed as in any way limiting their scope.

The following abbreviations are used herein: NMR refers to nuclear magnetic resonance (spectroscopy); NMP refers to N-methyl-2-pyrrolidone; DMI refers to 1,3-dimethyl-2-imidazolidinone; TFA refers to trifluoroacetic acid; DBU refers to 1,8-diazabicyclo[5.4.0]undec-7ene; MSA refers to methanesulfonic acid; DIPEA refers to N,N-diisopropylethylamine, TEA refers to trimethylamine; $K_2CO_3$ refers to ytterbium(III) trifluoromethanesulfonate; $FeCl_3$ refers to iron(III) chloride; ML refers to mother liquor; NaOH refers to sodium hydroxide; $CsCO_3$ refers to cesium carbonate; Na 2 CO 3 refers to sodium carbonate; $K_2CO_3$ refers to potassium carbonate; $K_2HPO_4$ refers to dipotassium phosphate; $CuSO_4$-$6H_2O$ refers to copper sulfate hexahydrate; $KHCO_3$ refers to potassium bicarbonate; KOAc refers to potassium acetate; and qNMR refers to quantitative nuclear magnetic resonance.

HPLC Methods

Achiral high-performance liquid chromatography (HPLC) was used for batch and flow studies to determine the purity profile of samples throughout a reaction as well as after isolation. This method was also used to determine the concentration of samples for additional solubility studies as well as mass balance data.

Chiral stationary phase (e.g., normal phase) HPLC was used in batch as well as flow studies to determine the efficiency of the racemization process. This method was also used to determine the % ee of solids versus the supernatant. This information was useful for determining the eutectic point of the mixture as well as the efficiency of crystallization of compound A in solution (e.g., anisole).

An illustrative achiral reverse phase method used was as follows: column-ACE Excel Super® C18, 3 μm, 3×50 mm (Advanced Chromatography Technologies, Ltd., Aberdeen, Scotland); mobile phase A is 0.05% trifluoroacetic acid in water; mobile phase B is 0.05% trifluroacetic acid in acetonitrile; sample concentration of approximately 0.25 mg/mL; temperature –35° C.; flow rate of approximately 1.5 mL/min; UV detection at 215 nm (4 nm bandwidth) and/or 254 nm (8 nm bandwidth); injection volume 1 NL; run time 7.5 min; post time 1.5 min; gradient elution as follows: at time 0-95:5 A/B; time 4.5 min –0:100 A/B; time 7.5 min –0:100 NB.

An illustrative achiral reverse phase method used was as follows: column—Poroshell® 120 (4.6×150 mm, 2.7 μm) (Agilent, Santa Clara, California); column temperature 21° C.; mobile phase A is 20 mM ammonium formate in water; mobile phase B is acetonitrile; injection volume of 5 μL; flow rate of 0.9 mL/min; UV detection at 256 nm (4 nm bandwidth); gradient elution as follows: time 0 min –80:20 NB; time 10 min –25:75 A/B; time min –10:90 NB; time 13 min –10:90 A/B; time 13.1-80:20 NB; time 17 min –80:20 NB; sample tray temperature of 5° C.

A illustrative chiral normal phase method used was as follows: column—Chiralpak® IC-3 (4.6×100 mm, 3 μm) (Daicel Corp.); column temperature 40° C.; mobile phase A is n-heptane; mobile phase B is 1:1 methanol/ethanol; injection volume of 5 μL; flow rate of 1 mL/min; UV detection at 256 nm (4 nm bandwidth); isocratic elution as follows: time 0 min –75:25 A/B; time 10 min –75:25 NB; sample tray temperature of 2 to 8° C.

Example 1—Solvent Screening Studies

Several solvents were evaluated for suitability in a process for racemizing (P)-compound A or a salt thereof. Compositions containing (P)-compound A or (M)-compound A and solvent were prepared or obtained and heated as indicated. The results are summarized in Tables 1-3, where LCAP is liquid chromatography area percent—a measurement of the amount of a substance (e.g., compound A) in the reaction mixture.

TABLE 1

Solvent studies for racemization[1] of (P)-compound A

| Solvent | bp (° C.) | % ee | Cpd A (LCAP) | LCAP Impurities |
|---|---|---|---|---|
| NMP | 202 | n/a | 16.41 | 75.87% [2] |
| sulfolane | 285 | 75.52 | 86.27 | 7.97% [2] |
| cyrene | 227 | — | — | Solvent decomposed |
| diphenyl ether | 258 | 69.10 | 97.52 | No single impurity >1% |
| DMI | 225 | 61.14 | 59.58 | Numerous new impurities from 4 to 20% |
| 1-octadecene | 315 | 74.22 | 98.46 | No single impurity >0.5% (0.44 mg/mL at 20° C.) |

[1]feedstock was (P)-compound A having 99.57% ee; reaction was heated to 250° C. for 4 h

[2] 6-fluoro-7-hydroxy-1-(2-isopropyl-4-methylpyridin-3-yl)pyrido[2,3-d]pyrimidine-2,4 (1H,3H)-dione

TABLE 2

Solvent polarity and temperature studies for racemization of (M)- and (P)-compound A in NMP, sulfolane, or toluene

| Starting Compound | Solvent[1] | Temp. (° C.) | Time (h) | Additive (equiv) | % ee | Cpd A (LCAP) | LCAP Impurities |
|---|---|---|---|---|---|---|---|
| (M)-compound A | NMP | 250 | 3.5 | — | n/a | 16.41 | 75.87%[2] |
| (M)-compound A | NMP | 250 | 3.5 | TFA (1.5) | n/a | 7.64 | 80.10%[2] |
| (M)-compound A | NMP | 250 | 3.5 | DBU (1.5) | n/a | 0.57 | 69.38% m/z 445.19 (RT = 7.4); 17.01%[3] |
| (M)-compound A | NMP | 250 | 3.5 | MSA (1.5) | n/a | 0.78 | Solvent evaporation; 84.01%[2] |

TABLE 2-continued

Solvent polarity and temperature studies for racemization of (M)- and (P)-compound A in NMP, sulfolane, or toluene

| Starting Compound | Solvent[1] | Temp. (° C.) | Time (h) | Additive (equiv) | % ee | Cpd A (LCAP) | LCAP Impurities |
|---|---|---|---|---|---|---|---|
| (M)-compound A | NMP | 250 | 3.5 | 6N NaOH (1.5) | n/a | 2.53 | Solvent evaporation; 47.94%[2] and others |
| (P)-compound A[4] | NMP | 200 | 2 | — | 99.06 | 94.4 | Minimal decomp. at 0.19 wt% water |
| (P)-compound A[4] | NMP | 200 | 8 | — | 96.34 | 80.27 | 18.62%[2] |
| (P)-compound A[4] | NMP | 200 | 1 | DIPEA (1.5) | 99.25 | 83.95 | No single major new impurity |
| (P)-compound A[4] | NMP | 200 | 1 | TEA (1.5) | n/a | 65.26 | Multiple new impurities |
| (P)-compound A[4] | NMP | 200 | 1 | DBU (1.5) | n/a | 0.96 | 81.69% m/z 445.19 (RT = 7.4); 14.33%[3] |
| (P)-compound A[4] | NMP | 200 | 1 | $Yb(OTf)_3$ (0.25) | 99.33 | 91.98 | 5.97%[2] |
| (P)-compound A[4] | NMP | 200 | 1 | $FeCl_3$ (0.25) | 99.53 | 92.99 | 4.90%[2] |
| (P)-compound A[4] | NMP | 200 | 1 | Montmorillonite (50 wt %) | 99.60 | 94.23 | 5.11%[2] |
| (P)-compound A[4] | sulfolane | 200 | 71 | — | 86.07 | 90.28 | 6.40%[2] |
| (P)-compound A[4] | sulfolane | 280 | 3.5 | — | 50.89 | 76.06 | 12.32%[2] |
| (P)-compound A[4] | toluene | 200 | 71 | — | 83.04* | 58.66 | 36.31%[2] |

[1]Ten volumes of solvent
[2]6-fluoro-7-hydroxy-1-(2-isopropyl-4-methylpyridin-3-yl)pyrido[2,3-d]pyrimidine-2,4(1H,3H)-dione
[3]unidentified impurity
[4](P)-compound A had 99.57% ee

TABLE 3

Solvent evaluation for racemization of (P)-compound A

| Solvent[1] | Temp (° C.) | Time (h) | % ee | Cpd A (LCAP) | LCAP Impurities |
|---|---|---|---|---|---|
| NMP | 200 | 8 | 92.68 | 80.27 | 18.62% [2] |
| NMP | 250 | 4 | n/a | 16.41 | Significant decomposition |
| sulfolane | 250 | 4 | 51.04 | 86.27 | 7.97% [2] |
| sulfolane | 280 | 4 | 1.78 | 76.06 | 12.32% [2] |
| diphenyl ether | 250 | 4 | 38.2 | 97.52 | No single impurity >1% |
| DMI | 250 | 4 | 22.28 | 59.58 | Numerous new impurities from 4-20% |
| 1-octadecene | 250 | 4 | 48.44 | 98.46 | No single impurity >0.5% (0.44 mg/mL at 20° C.) |
| Anisole[3] | 300 | 10 min | 4 | 99 | 4% ee after cooling to ambient temperature and stirring for 36 h |

[1]Ten volumes of solvent were used
[2] 6-fluoro-7-hydroxy-1-(2-isopropyl-4-methylpyridin-3-yl)pyrido[2,3-d]pyrimidine-2,4(1H,3H)-dione
[3]Thirty volumes of solvent were used These results demonstrate the suitability of diphenyl ether, 1-octadecene, and anisole as solvents for racemizing (P)-compound with minimal thermal decomposition. Moreover, using toluene, NMP, or sulfolane as solvents resulted in decomposition of compound A and/or minimal racemization at 250° C.

In addition, the results demonstrate that anisole not only provides minimal thermal decomposition, even after stirring for 36 h, but also provides both high stereochemical purity and chemical purity.

Additional solvent screening further identified anisole as a suitable solvent due to the high solubility of (P)-compound A, lower solubility of compound A, and low vapor pressure. The combination of these physical properties enabled the process to be run at moderate pressures. These results are shown in Table 4.

TABLE 4

Solubility of (P)-compound A at 22° C.

| Solvent | Incubation (h) | Solubility (mg/mL) |
|---|---|---|
| anisole | 22 | 163-202 |
| 1,2-dichlorobenzene | 22 | 196 |
| diphenyl ether | 22 | 92 |
| dibenzyl ether | 22 | 97 |
| diphenyl ether | 22 | 63 |
| anisole | 69 | 186 |

The suitability of heptane as an antisolvent for crystallization was evaluated using compound A (99.1 wt. %). The results are shown in Table 5.

TABLE 5

Solubility of compound A in anisole with anti-solvent heptane

| Anisole:heptane (v/v) | Solubility of compound A (mg/mL) |
|---|---|
| 100:0 | 69 |
| 67:33 | 25 |
| 50:50 | 14 |
| 33:67 | 4 |
| 100:0 | 18[4] |

[4]after cooling and stirring crude compound A/anisole slurry at ambient temperature for approximately 48 h Heptane reduced the solubility of compound A with increasing amounts of heptane. It was subsequently observed that compound A's solubility in pure anisole was lower than 69 mg/mL (about 18 mg/mL) at ambient temperature indicating the existence of a less soluble more thermodynamically stable crystal form. These results indicate that a cooling crystallization could also be used to isolate compound A.

Example 2

A (P)-compound A solution was prepared by extraction of (P)-compound A from a 88:12 PIM solid mixture using anisole at room temperature to yield a 10 wt. % (P)-compound A solution and a solid phase containing compound A as a racemate. The solid and liquid phases were separated by filtration and the resulting liquid was racemized at 315° C. and 2.5 MPa in approximately 10 minutes. Following racemization, the product was recovered by cooling crystallization in anisole. Solid compound A was used to seed the crystallization. The overall process yield was 77% and yielded crystallized product containing less than 10 wt. % impurities.

Example 3

A composition comprising (P)-compound A (1.48 kg (P)-compound A) was prepared in a semi-continuous process by diluting feedstock comprising (P)-compound A (14.72 kg) with 1.4 L of anisole. The feedstock was passed through a 100 micron filter to reject solids prior to conveying the feedstock using a gear pump and check valve. After passing through the check valve, the mixture was preheated in a tube-in-tube heat exchanger at a set point of 315° C. and then pumped at an average flow rate of 80 g/min over a period of 3.25 hours through a tube-in-tube flow reactor (1 L volume) heated to a set point of 315-320° C. The converted crude product was cooled using a tube-in-tube heat exchanger prior to letting down pressure and conveying the crude product stream to a jacketed reactor (120° C.) for crystallization. The cooler had a set point of 120° C., and the downstream equipment was heat-traced to maintain the product at a minimum of 120° C. and thus avoid product crystallization in the equipment. The cooled crude product stream was passed through a 100 micron filter to reject solids prior to conveying it through a backpressure regulator (2.55 MPa) to maintain pressure in the system. A series of pressure and temperature transducers were employed to monitor system conditions, and a mass flow meter was placed after the gear pump to monitor flow and allow control through a flow transmitter and controller coupled to the gear pump. A high-pressure rupture disc was installed in case of unexpected system overpressure, designed to divert the stream for safe capture and remedial handling.

The process provided a bulk racemized product of 53.3% (P)-compound A and 46.7% (M)-compound A before crystallization. The collected crude product was cooled to 90° C. and seeded with compound A (380 g). After seeding, the temperature was lowered to 10° C. (0.1° C./min) and maintained for 16 hours. The temperature was then lowered to 0° C. and maintained for 30 hours. The material was then vacuum filtered from the reaction vessel, and the collected solid cake was washed with anisole (1.5 L), dried at 60-70° C. for 72 hours to provide 1.43 kg of 99.2% achiral purity compound A having a PIM ratio of 50.5/49.5, giving an isolated yield of 76.9%.

In other instances, solid (P)-compound A (1.93 kg, 88:12 PIM) was suspended in anisole (5 L/kg). The slurry was separated by filtration to generate a solution of (P)-compound in anisole and a solid phase comprised of compound A (0.38 kg). Additional anisole was added to the solution of (P)-compound A to achieve a potency of 10 wt %. The feedstock was passed through a 100 micron filter to reject solids prior to conveying the feedstock using a gear pump and check valve. After passing through the check valve, the mixture was preheated in a tube-in-tube heat exchanger at a set point of 315° C. and then pumped at an average flow rate of 80 g/min over a period of 3.25 hours through a tube-in-tube flow reactor (1 L volume) heated to a set point of 315-320° C. The converted crude product was cooled using a tube-in-tube heat exchanger prior to letting down pressure and conveying the crude product stream to a jacketed reactor (120° C.) for crystallization. The cooler had a set point of 120° C., and the downstream equipment was heat-traced to maintain the product at a minimum of 120° C. and thus avoid product crystallization in the equipment. The cooled crude product stream was passed through a 100 micron filter to reject solids prior to conveying it through a backpressure regulator (2.55 MPa) to maintain pressure in the system. A series of pressure and temperature transducers were employed to monitor system conditions, and a mass flow meter was placed after the gear pump to monitor flow and allow control through a flow transmitter and controller coupled to the gear pump. A high-pressure rupture disc was installed in case of unexpected system overpressure, designed to divert the stream for safe capture and remedial handling.

Example 4

The batch reactions were performed in a 25 mL Parr 5500 reactor system. (P)-compound A (520 mg) (>99% ee) was dissolved in 15 mL anisole (approximately 30 volumes) and heated to 300° C. The reactor reached 300° C. in approximately 55 minutes and was maintained at this temperature for approximately 10 minutes before cooling the reactor down to ambient temperature. The reaction was periodically sampled, and the samples were analyzed using chiral HPLC. After cooling and stirring the mixture at ambient temperature for 36 hours, the product showed 4% ee.

Additional batch reactions were conducted using 5 volumes of anisole. The reaction mixtures of (P)-compound A (>99% ee) were heated to 300° C. for approximately 15 minutes before cooling to ambient temperature. After stirring at ambient temperature overnight, the mixture was found to show 2% ee. However, compared with the more dilute reaction, the more concentrated reaction mixture showed higher amounts of impurities with approximately 91% compound A compared with 99% in the first reaction.

Example 5— Base Screening Studies for Tartrate Extraction

Several inorganic bases were qualitatively assessed for the ability to solubilize/remove a tartrate in aqueous solution.

In summary, seven vessels were each charged with 2 mL of an aqueous base solution and DBTA was added in 25-50 mg increments until a solid precipitate persisted. The results are summarized in Tables 6 and 7.

TABLE 6

Solubility of DBTA in aqueous solutions

| Base | Visual solubility (mg/mL) | Observations |
| --- | --- | --- |
| NaOH (1N) | >150 | possible formation of 6-fluoro-7-hydroxy-1-(2-isopropyl-4-methylpyridin-3-yl)pyrido[2,3-d]pyrimidine-2,4(1H,3H)-dione under these conditions |

TABLE 6-continued

| Solubility of DBTA in aqueous solutions | | |
|---|---|---|
| Base | Visual solubility (mg/mL) | Observations |
| $CsCO_3$ (15 wt %) | 75 | |
| $Na_2CO_3$ (15 wt %) | 75-100 | gels after 1 h aging |
| $K_2CO_3$ (10 wt %) | >150 | pH drops from 10 to 7 in last 50 mg charge, with vigorous bubbling |
| $K_2HPO_4$ (15 wt %) | 125-150 | |
| $CuSO_4$•$6H_20$ (15 wt %) | <25 | |
| water | <25 | |

In addition, several potassium bases were qualitatively assessed for the ability to solubilize/remove DBTA from mother liquor (ML) feedstock comprising (P)-compound A and an organic solvent obtained from a conventional chiral resolution of compound A.

In summary, solutions of potassium bicarbonate, potassium carbonate, dipotassium phosphate, and potassium acetate were prepared and mixed with various amounts of the mother liquor, as listed in Table 7. After mixing, the compositions were visually inspected for the presence of insoluble material.

TABLE 7

| Evaluation of potassium bases | |
|---|---|
| Base | Ratio ML/aq (v/v) |
| 10 wt. % $KHCO_3$ | 2:1 |
| 20 wt. % $KHCO_3$ | 2:1 |
| 20 wt. % $KHCO_3$ | 1:1 |
| 20 wt. % $K_2CO_3$ | 2:1 |
| 35 wt. % $K_2CO_3$ | 2:1 |
| 50 wt. % $K_2CO_3$ | 2:1 |
| 20 wt. % $K_2HPO_4$ | 2:1 |
| 40 wt. % $K_2HPO_4$ | 2:1 |
| 20 wt. % KOAc | 1:1 |
| 20 wt. % KOAc | 2:1 |
| 40 wt. % KOAc | 2:1 |

The results from the visual inspection indicated that the potassium bicarbonate and potassium carbonate solutions had the least amount of insoluble material, particularly the compositions containing 20 wt. % of the potassium base. More particularly, the compositions comprising 20 wt. % potassium bicarbonate and 1:1 ML/aq. ratio and 20 wt. % potassium carbonate and 2:1 ML/aq. exhibited good solubility performance.

Further, the effectiveness of aqueous potassium carbonate to solubilize and extract DBTA from an organic phase, mother liquor (ML) containing (P)-compound A was evaluated. Four concentrations of aqueous potassium carbonate (Compositions 1-4), as well as different volumetric ratios of aqueous phase to organic phase (ratios A-C), were assessed as shown in Table 8.

Solutions of 5-20 wt. % $K_2CO_3$ were prepared and mixed with the mother liquor comprising (P)-compound A, tartrate, and organic solvent in the volumetric ratios listed in Table 8. After mixing, each of the compositions were analyzed by HPLC to determine the concentration of (P)-compound A in the aqueous and organic phases. The results are summarized in Table 8.

TABLE 8

| Evaluation of potassium carbonate | | | | | |
|---|---|---|---|---|---|
| | | $K_2CO_3$ | | | |
| (P)-cpd A (mg/mL) | | 5 wt. % (Comp. 1) | 10 wt. % (Comp. 2) | 15 wt. % (Comp. 3) | 20 wt. % (Comp. 4) |
| volumetric ratio (ML/Aq) | 0.5:1 (ratio A) | aq = 4.4 mg/mL<br>ML = 51.6 mg/mL | aq = 13.4 mg/mL<br>ML = 16.0 mg/mL | aq = 15.1 mg/mL<br>ML = 5.8 mg/mL | aq = 16.2 mg/mL<br>ML = 3.4 mg/mL |
| | 1:1 (ratio B) | Solids & off-gassing | aq = 6.2 mg/mL<br>ML = 39.2 mg/mL | aq = 9.9 mg/mL<br>ML = 37.0 mg/mL | aq = 24.3 mg/mL<br>ML = 11.5 mg/mL |
| | 2:1 (ratio C) | Solids & off-gassing | Solids & off-gassing | aq = 7.0 mg/mL<br>ML = 45.6 mg/mL | aq = 5.9 mg/mL<br>ML = 44.8 mg/mL |

DBTA was not detectable in any of the organic phases that were analyzed by HPLC. Moreover, many of the compositions advantageously provided, after mixing, solutions with substantially no solids and clean phase separation between the organic and aqueous phases. However, as shown in Table 8, Compositions 1B, 10, and 2C comprising 5-10 wt. % potassium carbonate and the relatively higher/highest amounts of organic phase, resulted in undesirable mixtures of solids. In contrast, each of the other compositions exhibited no solids and presented clean phase cuts between the organic and aqueous phases after mixing. Moreover, Compositions 1A, 2B, 3B, 3C, and 4C desirably exhibited relatively low levels of (P)-compound A in the aqueous phases. In addition, Compositions 2B, 3B, 3C, and 4C also desirably required lower relative volumes of aqueous phase, which would facilitate processing by permitting smaller volume reactors.

Moreover, it was determined during these screening studies that using $K_2CO_3$ to extract the MeTHF/heptane residual liquor from the AMG 510 synthesis, provided a clean phase-cut between the lower aqueous phase containing (+)-DBTA and the upper organic phase containing (P)-compound A. The methyltetrahydrofuran (MeTHF), which typically is a solvent used in large volumes in the AMG 510 synthesis, is partial miscibility in water and causes (P)-compound A to partition into the first extracted aqueous stream from $K_2CO_3$ treatment. It has been discovered that the presence of (P)-compound A compromises the quality grade of (+)-DBTA.

Example 6

Recycling of DBTA from aqueous solution ensures continuous supply of (+)-DBTA with required chiral purity specification. In (M)-Compound A classical resolution crystallization, 3.0 equiv. of (+)-DBTA are added and only 0.5 equiv. are used in (M)-Compound A co-crystal.

Using a workstream from isolated (P)-compound A, the residual aqueous liquor (pH=9-10) containing (+)-DBTA) in $K_2CO_3$ 15 wt. % (1.6 equiv. in 4.2 vol water) was treated with hydrochloric acid (HCl) to recover the desired (+)-DBTA). In a vessel jacketed vessel, a HCl solution was prepared with 30.0 equiv. of the acid and water (4.2 vol). The jacket warmth to 45° C., the (+)-DBTA/$K_2CO_3$ aqueous solution was careful dosed over 2 hours to the HCl solution as effervescence was observed, and white solid slurry appeared. At the end of the addition, the slurry was cooled to 10° C. over a period of 5 hours. Filtration provided (D)-DBTA monohydrate crystals which were washed with water (8.8 vol). Once dried under vacuum at 40° C., the isolated monohydrate (+)-DBTA) was recovered at 93% with a purity of 99.5 wt. % and chiral purify of 100% ee, ready to be used for the next (M)-compound A classical resolution crystallization.

The stereochemical purity was analyzed using chiral HPLC using the following conditions: HPLC column, Chiralpak IC-3, 3 μm, 4.6×100 mm (Chiral Technologies, Inc., Catalog #83523); a gradient pump, a temperature-controlled autosampler, a temperature-controlled column compartment, a UV detector with 10 mm flow cell (other size of flow cell may be used, provided the sensitivity requirement can be met), and a chromatography data system (e.g., Agilent 1200 or equivalent).

Reference standards and solvents were obtained as follows: (+)-dibenzoyl-D-tartaric acid (DBTA), CAS RN: 17026-42-5, TCI, Product Number: D3826; (−)-dibenzoyl-L-tartaric acid (DBTA), CAS RN: 2743-38-6, TCI, Product Number: D3492; methanol (MeOH), HPLC grade, (Sigma-Aldrich, Part #34860); ethanol (EtOH), 200 proof, (Decon Labs, Part #2701); n-Heptane 99%, HPLC grade (Sigma-Aldrich, Part #650536).

Stock solutions of (+)-DBTA) and (−)-DBTA) (approximately 0.5 mg/mL) were prepared in MeOH/Et0H 1:1 (v/v) as a diluent. Sample solutions were prepared containing approximately 5 mg/mL and 0.05 mg/mL of (+)-DBTA), respectively. Samples were analyzed under the following conditions: column temperature: 30° C.; isocratic mobile phase: 0.05% TFA/20% MeOH/Et0H (1:1)/80% heptane (v/v); flow rate: 0.8 mL/min; injection volume: 2 μL; UV detection at 230 nm; acquisition time: 6 min; and autosampler temperature: 10° C. Under these conditions, (+)-DBTA) had a retention time of approximately 2.52 min and L-DBTA had a retention time of approximately 4.01 min.

Example 7

This example demonstrates a process of the disclosure for isolating (+)-DBTA monohydrate free acid.

The procedure described in Example 6 was performed to provide (+)-DBTA-monohydrate (99.4 wt. % purity) with less than 1% lost into the residual liquor. Analysis of the crystal by mass spectrometry (e.g., inductively coupled plasma-mass spectrometry (ICP-MS)) reveals the presence of only trace amounts of potassium (e.g., 0.4 wt. %). The low potassium content confirms that the isolated (+)-DBTA is fully protonated, as shown in Table 9. The neutralization reaction occurring into this current disclosed invention: $K_2CO_3+HCl=H_2O+CO_2+KCl$, such that potassium chloride (KCl) coating the (+)-DBTA crystal is water washed into wet cake before drying.

TABLE 9

Analysis of isolated (+)-DBTA-monohydrate from the neutralization/crystallization process

| Substance | MW (g/mol) | Theoretical | Analysis Method | Experimental |
|---|---|---|---|---|
| Water | 18 | 4.8 wt. % | Karl Fischer | 4.3 wt. % |
| (+)-DBTA | 358.3 | 95.2 wt. % | qNMR | 95.1 wt. % |
| (+)-DBTA monohydrate | 376.3 | 100 wt. % | balance | 99.4 wt. % |

The prepared (+)-DBTA-monohydrate was used in a synthesis of AMG 510 with no detrimental impact on forming (M)-compound A by way of classical chiral resolution performance (yield, achiral/chiral purity). The presence of water saturated Me-THF does not impact the classical chiral resolution process and presents no risk.

All references, including publications, patent applications, and patents, cited herein are hereby incorporated by reference to the same extent as if each reference were individually and specifically indicated to be incorporated by reference and were set forth in its entirety herein.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

The use of the terms "a" and "an" and "the" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (for example, "such as") provided herein, is intended merely to better illuminate the invention and does not pose a limitation on the scope of the invention unless otherwise claimed. No language in the specification should be construed as indicating any non-claimed element as essential to the practice of the invention.

What is claimed:

1. A process comprising:

heating a composition comprising (P)-compound A:

((P)-compound A)

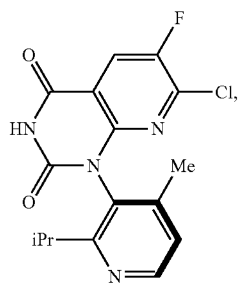

or a salt thereof and a solvent to a temperature of 250° C. to 350° C. to form racemized compound A:

(A)

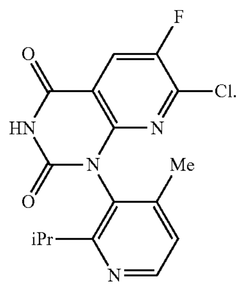

2. The process of claim 1, wherein the solvent comprises anisole.

3. The process of claim 1, wherein the composition is heated to a temperature of 305° C. to 320° C.

4. The process of claim 1, wherein the heating is performed at a pressure of 1.7 to 7.0 MPa.

5. The process of claim 1, wherein (P)-compound A has a % ee of 75% or more in the composition prior to heating.

6. The process of claim 1, wherein racemized compound A has a % ee of 50% or less.

7. The process of claim 1, wherein racemized compound A, after heating, comprises less than 10 wt % of impurities as determined by chromatography.

8. The process of claim 1, wherein the heating occurs for 1 hour to 4 hours.

9. The process of claim 1, further comprising subjecting the racemized compound A to a chiral resolution using a tartrate to separate (P)-compound A and (M)-compound A:

((M)-compound A)

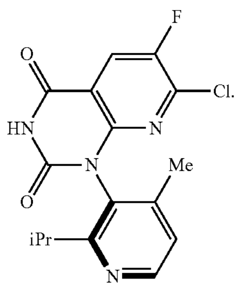

10. The process of claim 9, further comprising converting the (M)-compound A to AMG 510;

(AMG 510)

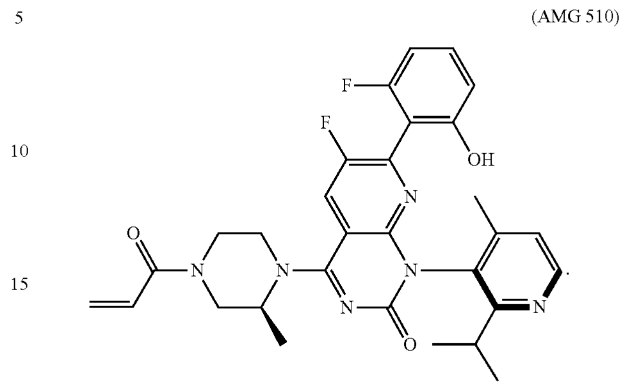

11. The process of claim 1, wherein the solvent comprises a nonpolar solvent.

12. The process of claim 1, wherein the solvent is selected from the group consisting of diphenyl ether, 1-octadecene, anisole, and a combination thereof.

13. The process of claim 1, wherein the composition is heated to a temperature of 300° C. to 325° C.

14. The process of claim 1, wherein the temperature is 310° C.

15. The process of claim 1, wherein the temperature is 315° C.

16. The process of claim 1, wherein (P)-compound A has a % ee of 50% or more in the composition prior to heating.

17. The process of claim 1, wherein (P)-compound A has a % ee of 90% or more in the composition prior to heating.

18. The process of claim 1, wherein racemized compound A has a % ee of 30% or less.

19. The process of claim 1, wherein racemized compound A, after heating, comprises less than 5 wt % of impurities as determined by chromatography.

20. The process of claim 1, wherein racemized compound A, after heating, comprises less than 2 wt % of impurities as determined by chromatography.

21. The process of claim 1, wherein the heating occurs for 5 minutes to 12 hours.

22. The process of claim 1, further comprising subjecting the racemized compound A to simulated moving bed chromatography to separate (P)-compound A and (M)-compound A.

23. The process of claim 1, wherein, prior to heating the composition comprising (P)-compound A or a salt thereof and a solvent, the composition comprising (P)-compound A or a salt thereof is prepared from a starting composition comprising (P)-compound A, a tartrate, and an organic solvent by admixing the starting composition and an aqueous solution of a base to remove the tartrate and providing the composition comprising (P)-compound A or a salt thereof.

24. The process of claim 23, wherein the tartrate is (+)-DBTA
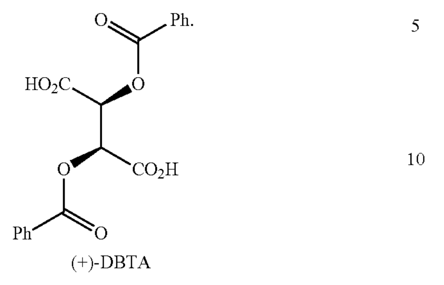
(+)-DBTA
25. The process of claim 24, wherein the base is selected from the group consisting of sodium hydroxide, sodium carbonate, potassium carbonate, dipotassium phosphate, and a combination thereof.
26. The process of claim 1, wherein the solvent is anisole.
* * * * *